US006381577B1

(12) United States Patent
Brown

(10) Patent No.: US 6,381,577 B1
(45) Date of Patent: Apr. 30, 2002

(54) MULTI-USER REMOTE HEALTH MONITORING SYSTEM

(75) Inventor: Stephen J. Brown, San Mateo, CA (US)

(73) Assignee: Health Hero Network, Inc., Mountain View, CA (US)

(*) Notice: Subject to any disclaimer, the term of this patent is extended or adjusted under 35 U.S.C. 154(b) by 0 days.

(21) Appl. No.: 09/517,140

(22) Filed: Mar. 2, 2000

Related U.S. Application Data

(63) Continuation of application No. 08/975,774, filed on Nov. 21, 1997, now Pat. No. 6,101,878, which is a continuation of application No. 08/847,009, filed on Apr. 30, 1997, now Pat. No. 5,897,493.
(60) Provisional application No. 60/041,746, filed on Mar. 28, 1997, and provisional application No. 60/041,751, filed on Mar. 28, 1997.

(51) Int. Cl.[7] .............................................. G06F 17/60
(52) U.S. Cl. ........................................................ 705/2
(58) Field of Search ............................ 705/2, 3, 10, 14, 705/41; 600/300, 301

(56) References Cited

U.S. PATENT DOCUMENTS

| 5,128,752 A | * | 7/1992 | Von Kohorn | 705/10 |
| 5,262,943 A | * | 11/1993 | Thibado et al. | 600/300 |
| 5,299,121 A | * | 3/1994 | Brill et al. | 600/301 |

(List continued on next page.)

FOREIGN PATENT DOCUMENTS

| EP | 0251520 | * | 6/1987 |
| EP | 0370599 | * | 7/1989 |
| WO | 9509386 | * | 4/1995 |
| WO | 9520199 | * | 7/1995 |
| WO | 9708605 | * | 3/1997 |
| WO | 9712544 | * | 4/1997 |

OTHER PUBLICATIONS

Giuffrida, A; Should we pay the patient? Review of financial incentives to enhance patient compliance; Biomedical Journal, vol. 315, pp. 703–707, 1997.*

Reis, H; Telemedicine: transmitting expertise to the point of care; Toward an Electronic patient record, vol. 3, 1997; Apr. 27–May 3, 1997, pp. 248–256.*

*Primary Examiner*—James P. Trammell
*Assistant Examiner*—Thomas A. Dixon
(74) *Attorney, Agent, or Firm*—Black Lowe & Graham PLLC

(57) ABSTRACT

The invention presents a networked system for identifying an individual, communicating information to the individual, and remotely monitoring the individual. The system includes a server and a workstation for entering in the server queries to be answered by the individual. The server is preferably a web server and the workstation is preferably a personal computer or remote terminal connected to the server via the Internet. The system also includes a remotely programmable apparatus connected to the server via a communication network, preferably the Internet. The remotely programmable apparatus interacts with the individual in accordance with a script program received from the server. The server includes a script generator for generating the script program from the queries entered through the workstation. The script program is received and executed by the remotely programmable apparatus identify the individual, to communicate the queries to the individual, to receive responses to the queries, and to transmit the responses from the remotely programmable apparatus to the server. Identification of the individual can also be achieved via a data card, a remote monitoring device, or the interception of data from a separate information system. As the present invention has multi-user capabilities, it can be used in a public place, such as a pharmacy or health care clinic. The multi-user capabilities also allow collection and tracking of user data for the healthcare industry.

7 Claims, 20 Drawing Sheets

U.S. PATENT DOCUMENTS

| | | | | |
|---|---|---|---|---|
| 5,329,459 A | * | 7/1994 | Kaufman et al. | 700/242 |
| 5,339,821 A | | 8/1994 | Fujimoto | 128/700 |
| 5,390,238 A | * | 2/1995 | Kirk et al. | 379/106.02 |
| 5,410,471 A | * | 4/1995 | Alyfuku et al. | 600/300 |
| 5,434,611 A | * | 7/1995 | Tamura | 725/116 |
| 5,441,047 A | * | 8/1995 | David et al. | 600/483 |
| 5,454,721 A | | 10/1995 | Kuch | 434/127 |
| 5,544,649 A | * | 8/1996 | David et al. | 600/301 |
| 5,558,638 A | * | 9/1996 | Evers et al. | 604/66 |
| 5,572,421 A | * | 11/1996 | Altman et al. | 705/3 |
| 5,619,991 A | * | 4/1997 | Sloane | 600/300 |
| 5,642,731 A | * | 7/1997 | Kehr | 600/300 |
| 5,828,943 A | * | 10/1998 | Brown | 434/258 |
| 5,893,098 A | * | 4/1999 | Peters et al. | 707/10 |
| 6,022,615 A | * | 2/2000 | Iliff | 600/300 |
| 6,151,586 A | * | 11/2000 | Brown | 705/14 |
| 6,177,940 B1 | * | 2/2001 | Bond et al. | 345/352 |
| 6,189,029 B1 | * | 2/2001 | Fuerst | 705/10 |

* cited by examiner

SCRIPT ENTRY SCREEN — 56

SCRIPT NAME: DIABETES SCRIPT 1 — 92

QUERIES — 94

| | CHOICE 1 | CHOICE 2 | CHOICE 3 | CHOICE 4 — 96 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)

98 — ☒ GLUCOSE METER ☐ RESPIRATORY FLOW METER ☐ BP CUFF

CONNECTION TIME: 03:00 ▽ — 100 | CREATE SCRIPT — 102 | CANCEL — 104

*FIG. 5*

NUMBER: 9001 {LF}

LED: 1 {LF}

ZAP: {LF}

CLS: {LF}

DISPLAY: PLEASE ENTER IN ID CODE, INSERT SMART
CARD, OR CONNECT MONITORING DEVICE {LF}

WAIT: {LF}

CLS: {LF}

DISPLAY: ANSWER QUERIES NOW?
PRESS ANY BUTTON TO START {LF}

WAIT: {LF}

CLS: {LF}

DISPLAY: HOW DO YOU FEEL?

VERY          VERY
      BAD  BAD  GOOD  GOOD {LF}

INPUT: OOOO {LF}

CLS: {LF}

DISPLAY: HOW WELL ARE YOU
MANAGING YOUR DISEASE?
VERY             VERY
WELL  BADLY  WELL  WELL {LF}

INPUT: OOOO {LF}

CLS: {LF}

DISPLAY: HOW HARD IS IT FOR YOU TO
FOLLOW YOUR TREATMENT PLAN?
VERY             VERY
HARD  HARD  EASY  EASY {LF}

*FIG. 6A*

INPUT: OOOO {LF}

CLS: {LF}

DISPLAY: HOW HARD IS IT FOR YOU TO
        CONTROL YOUR BLOOD SUGAR?
        VERY                   VERY
        HARD   HARD  EASY  EASY {LF}

INPUT: OOOO {LF}

CLS: {LF}

DISPLAY: CONNECT GLUCOSE METER
        AND PRESS ANY BUTTON
        WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

DISPLAY: CONNECT APPARATUS TO
        TELEPHONE JACK AND
        PRESS ANY BUTTON
        WHEN FINISHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

*FIG. 6B*

SCRIPT ASSIGNMENT SCREEN

AVAILABLE SCRIPTS:   PATIENTS:

[X] DIABETES SCRIPT 1   [X] JANE DOE
[ ] DIABETES SCRIPT 2   [ ] JOHN SMITH
[ ] ASTHMA SCRIPT 1    [ ] TYPE: DIABETES

[ ADD SCRIPT ]   [ ASSIGN SCRIPT ]   [ DELETE SCRIPT ]

*Fig. 7*

HOW DO YOU FEEL?

VERY BAD   BAD   GOOD   VERY GOOD

*Fig. 8*

CONNECT GLUCOSE METER AND PRESS ANY BUTTON WHEN FINISHED

*Fig. 9*

PATIENT REPORT

PATIENT: DOE, JANE ▽        DATE OF MEASUREMENT: MARCH 15, 1997 ▽

QUERY RESPONSES

HOW DO YOU FEEL?
BAD

HOW WELL ARE YOU MANAGING YOUR DISEASE?
BADLY

HOW HARD IS IT FOR YOU TO FOLLOW YOUR TREATMENT PLAN?
HARD

HOW HARD IS IT FOR YOU TO CONTROL YOUR BLOOD SUGAR?
VERY HARD

*FIG. 10*

MULTI-USER REMOTE HEALTH MONITORING SYSTEM

RELATED APPLICATIONS

This application is a Continuation of U.S. Ser. No. 08/975,774 filed Nov. 21, 1997 now U.S. Pat. No. 6,101,878 issued Aug. 8, 2000, which is a continuation U.S. Ser. No. 08/847,009 filed Apr. 30, 1997, now U.S. Pat. No. 5,897,493 issued Apr. 27, 1999 which claims priority from Provisional Application Ser. No. 60/041,746 filed Mar. 28, 1997 and from Provisional Application Ser. No. 60/041,751 filed Mar. 28, 1997. All of the above named applications are hereby incorporated by reference.

FIELD OF THE INVENTION

This invention relates generally to remote health monitoring systems. In particular, it relates to a multi-user remote health monitoring system which is capable of identifying a particular user in a number of different ways. The multi-user remote health monitoring system can also be used for tracking and collecting patient data.

BACKGROUND OF THE INVENTION

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Unfortunately, no convenient and cost effective monitoring system exists for the patients who have the greatest need for monitoring, namely the poor and the elderly.

Prior attempts to monitor patients remotely have included the use of personal computers and modems to establish communication between patients and healthcare providers. However, computers are too expensive to give away and the patients who already own computers are only a fraction of the total population. Further, the patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the Internet and internet terminals. Although internet terminals are somewhat less costly than personal computers, they are still too expensive to give away to patients. Moreover, monthly on-line access charges are prohibitive.

Other attempts to monitor patients remotely have included the use of medical monitoring devices with built-in modems. Examples of such monitoring devices include blood glucose meters, respiratory flow meters, and heart rate monitors. Unfortunately, these monitoring devices are only designed to collect physiological data from the patients. They do not allow flexible and dynamic querying of the patients for other information, such as quality of life measures or psychosocial variables of illness. Another problem with such devices is that only the most self-motivated patients generate enough useful physiological data and call in regularly. Thus this method is not a good way to reach non-compliant patients.

Prior attempts to monitor patients remotely have also included the use of interactive telephone or video response systems. Such interactive systems are disclosed in U.S. Pat. No. 5,390,238 issued to Kirk et al. on Feb. 14, 1995, U.S. Pat. No. 5,434,611 issued to Tamura on Jul. 18, 1995, and U.S. Pat No. 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life and resistance to the monitoring grows over time.

Interactive telephone response systems, moreover, are generally incapable of collecting medical data from monitoring devices, such as blood glucose meters, respiratory flow meters, or heart rate monitors. In addition, patients tend to dislike the regular intrusion which decreases their compliance with the monitoring system.

Interactive video systems, on the other hand, cost around $20,000 for installation and are prohibitively expensive for the majority of patients. It is also difficult to identify each patient uniquely using this system.

A further disadvantage of these conventional interactive response systems is that they are aimed at a single user, thus preventing any multi-user capabilities. Interactive video response systems are too expensive to install for a single user. Interactive telephone response systems can be used for more than one member of a household, but it is often difficult to distinguish between the different patients. These characteristics, in conjunction with the fact that patients using the conventional interactive response systems do not usually exhibit regular use patterns, means that the patient data collected is statistically unreliable. Thus, these systems are not equipped to handle patient data collection and tracking.

Also, as conventional interactive response systems are intended for use in a patient's home, they are not suited for use in public areas. Their single user nature makes them ill-equipped to handle a large volume of users. Touch screen kiosks, which are commonly used in lobbies of public buildings to disseminate information, are difficult to individualize for a patient and are also very expensive. In addition, kiosks are self-contained and not designed to work with other separate information systems, such as the Internet or a healthcare provider's information system.

OBJECTS AND ADVANTAGES OF THE INVENTION

In view of the above, it is an object of the present invention to provide a simple and inexpensive system for identifying and remotely monitoring a plurality of patients. It is another object of the present invention to provide a remote monitoring system which incurs a minimal hardware cost per patient. It is another object of the present invention to communicate information to a plurality of patients. It is another object of the invention to provide a system which allows flexible and dynamic querying of a plurality of patients. Another object of the present invention is to allow automatic identification of an individual by use of data card, a remote monitoring device, or a separate information system. It is another object of the present invention to assign scripts to patients automatically. It is a further object of the present invention to allow the collection and tracking of data from a plurality of patients for statistical analysis. It is another object of the present invention to provide an interactive response system which accepts and uses input from separate information systems. A final object of the present invention is to provide individualized patient interaction at a public terminal without increasing administration costs.

These and other objects and advantages will become more apparent after consideration of the ensuing description and the accompanying drawings.

SUMMARY

The invention presents a networked system for remotely identifying and monitoring a plurality of individuals, and for communicating information to the individuals. The system includes a server, and a workstation for entering into the server query sets to be answered by the individuals. The server is preferably a world wide web server and the workstation is preferably a personal computer or network terminal connected to the web server via the Internet. The system also includes a remotely programmable apparatus for identifying and interacting with the individuals. The remotely programmable apparatus is connected to the server via a communication network, preferably the Internet. The remotely programmable apparatus interacts with the individuals in accordance with script programs received from the server.

The server includes a script generator for generating script programs from the query sets which are entered through the workstation. The script programs are executable by the remotely programmable apparatus to communicate the query sets to the individuals, to receive responses to the query sets, and to transmit the responses from the remotely programmable apparatus to the server. The server also includes a database connected to the script generator for storing the script program and the responses to the queries. The database also stores a list of individuals or individual types, and for each individual or individual type, has a pointer to at least one script program. The server also has script assignment means connected to the database, which assigns to an individual at least one script program, according to the script assignment information. The workstation allows a healthcare provider to enter in the script assignment information.

The remotely programmable apparatus has a communication device, such as a modem, for receiving the script programs from the server and for transmitting the responses to the server. The remotely programmable apparatus also has a user interface for communicating the query sets to the individuals and for receiving the responses to the query sets. In the referred embodiment, the user interface includes a display for displaying the query sets and user input buttons for entering the responses to the query sets. In an alternative embodiment, the user interface includes a speech synthesizer for audibly communicating the query sets and a speech recognizer for receiving spoken responses to the query sets.

The remotely programmable apparatus also includes a memory for storing the script programs and the responses to the query sets. The remotely programmable apparatus further includes a microprocessor connected to the communication device, the user interface, and the memory. The microprocessor executes the script programs to identify the individual, communicate the query sets to the individual, receive the responses to the query sets, and transmit the responses to the server through the communication network.

In one embodiment, the system also includes at least one monitoring device for producing measurements of a physiological condition of the individual and for transmitting the measurements to the apparatus. The monitoring device can also be used to help the remotely programmable apparatus identify the individual. The remotely programmable apparatus includes a device interface connected to the microprocessor for receiving the measurements from the monitoring device. The measurements are stored in the memory and transmitted to the server along with the individual's identity and the responses to the query sets. The server also preferably includes a report generator connected to the database for generating a report of the measurements and responses. The report is displayed on the workstation.

As the present invention has multi-user capabilities, it must identify each individual or individual type in order to select the correct script program. In one embodiment, the individual can enter his or her unique identification code into the remotely programmable apparatus. The code is sent to the server and used to determine which script program to send back to the apparatus.

In another embodiment, the system uses a data card, which contains information about an individual's identity. The remotely programmable apparatus includes a data card reader in which the data card can be placed and read. A personal identification number (PIN) can also be used in conjunction with the data card in order confirm an individual's identity. In this embodiment, the present invention resembles an ATM machine.

The system of the present invention can also identify an individual by intercepting data from a separate information system. Data sent from a server of the separate information system to a printer can pass through the remotely programmable apparatus, which can identify the individual and send the data to the server of the present invention. The data passing through the remotely programmable apparatus can also trigger a script program, which can display queries for the individual to answer, or send information to the printer to be printed. An example of this embodiment has the remotely programmable apparatus located in series between a pharmacy server and a pharmacy printer.

Finally, the multi-user characteristic of the present invention makes it possible to collect and track data on individuals. The information generated can be used in a number of ways—for demographic marketing reports for pharmaceutical companies or for epidemiological studies by health care providers.

BRIEF DESCRIPTION OF THE DRAWINGS

FIG. 5 is a script entry screen according to the preferred embodiment of the invention.

FIG. 6A is a listing of a sample script program according to the preferred embodiment of the invention.

FIG. 6B is a continuation of the listing of FIG. 6A.

FIG. 7 is a script assignment screen according to the preferred embodiment of the invention.

FIG. 8 is a sample prompt appearing on a display of the apparatus of FIG. 3.

FIG. 9 is a sample query displayed on a workstation of the system of FIG. 3.

FIG. 10 is a sample patient report displayed on the workstation of the system of FIG. 1.

DETAILED DESCRIPTION

The invention presents a system and method for remotely identifying and monitoring individuals, and for communicating information to the individuals. In a preferred embodiment of the invention, the individuals are patients and the system is used to collect data relating to the health status of the patients. The data can be used by healthcare providers or pharmaceutical companies for research or marketing purposes.

In the present invention, an individual is designated to mean a unique patient or a unique patient type, such as a diabetic. Also, it is to be understood that the invention is not limited to remote patient monitoring. The system and method of the invention may be used for any type of remote monitoring application. The invention may also be implemented as an automated messaging system for communicating information to individuals, as will be discussed in an alternative embodiment below.

Figure 1:
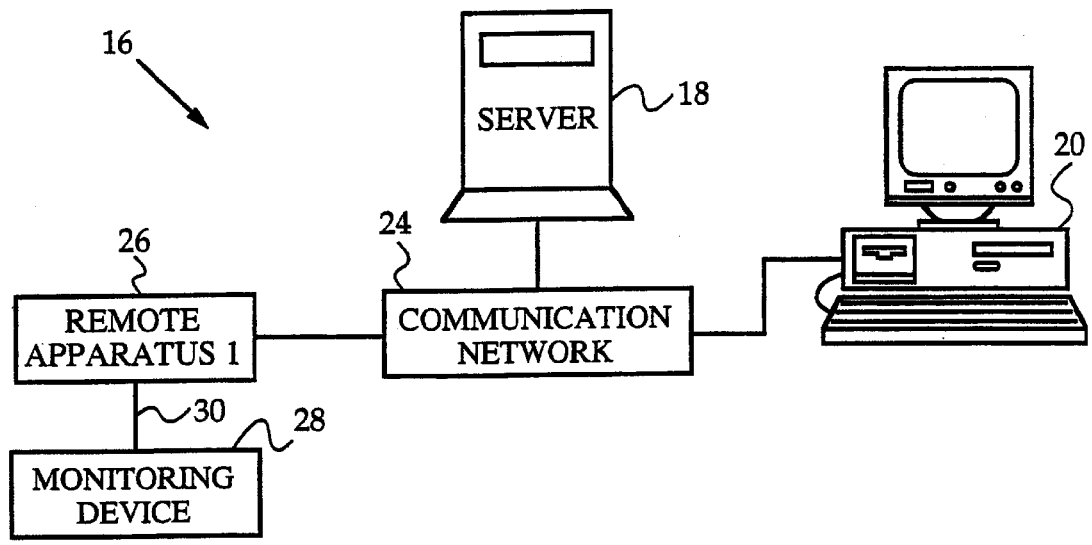
FIG. 1 is a block diagram of a networked system according to a preferred embodiment of the invention.

A preferred embodiment of the invention is illustrated in FIGS. 1–12. Referring to FIG. 1, a networked system 16 includes a server 18 and a workstation 20 connected to server 18 through a communication network 24. Server 18 is preferably a world wide web server and communication network 24 is preferably the Internet. It will be apparent to one skilled in the art that server 18 may comprise a single stand-alone computer or multiple computers distributed throughout a network. Workstation 20 is preferably a personal computer, remote terminal, or web TV unit connected to server 18 via the 25 Internet. Workstation 20 functions as a workstation for entering in server 18 messages and queries to be communicated to the patients.

System 16 also includes a remotely programmable apparatus 26 for monitoring patients. Apparatus 26 is designed to interact with a plurality of patients in accordance with script programs received from server 18. Apparatus 26 is in communication with server 18 through communication network 24, preferably the Internet. Alternatively, apparatus 26 may be placed in communication with server 18 via wireless communication networks, cellular networks, telephone networks, or any other network which allows apparatus 26 to exchange data with server 18. For clarity of illustration, only one apparatus 26 is shown in FIG. 1. It is to be understood that system 16 may include any number of apparatuses, with each apparatus used to monitor any number of patients.

In the preferred embodiment, each patient to be monitored is also provided with a monitoring device 28. Monitoring device 28 is designed to produce measurements of a physiological condition of the patient, record the measurements, and transmit the measurements to apparatus 26 through a standard connection cable 30. Examples of suitable monitoring devices 28 include blood glucose meters, respiratory flow meters, blood pressure cuffs, electronic weight scales, and pulse rate monitors. Such monitoring devices are well known in the art. The specific type of monitoring device provided to each patient is dependent upon the patient's disease. For example, diabetes patients are provided with a blood glucose meters for measuring blood glucose concentrations, asthma patients are provided with respiratory flow meters for measuring peak flow rates, obesity patients are provided with weight scales, etc.

Figure 2:
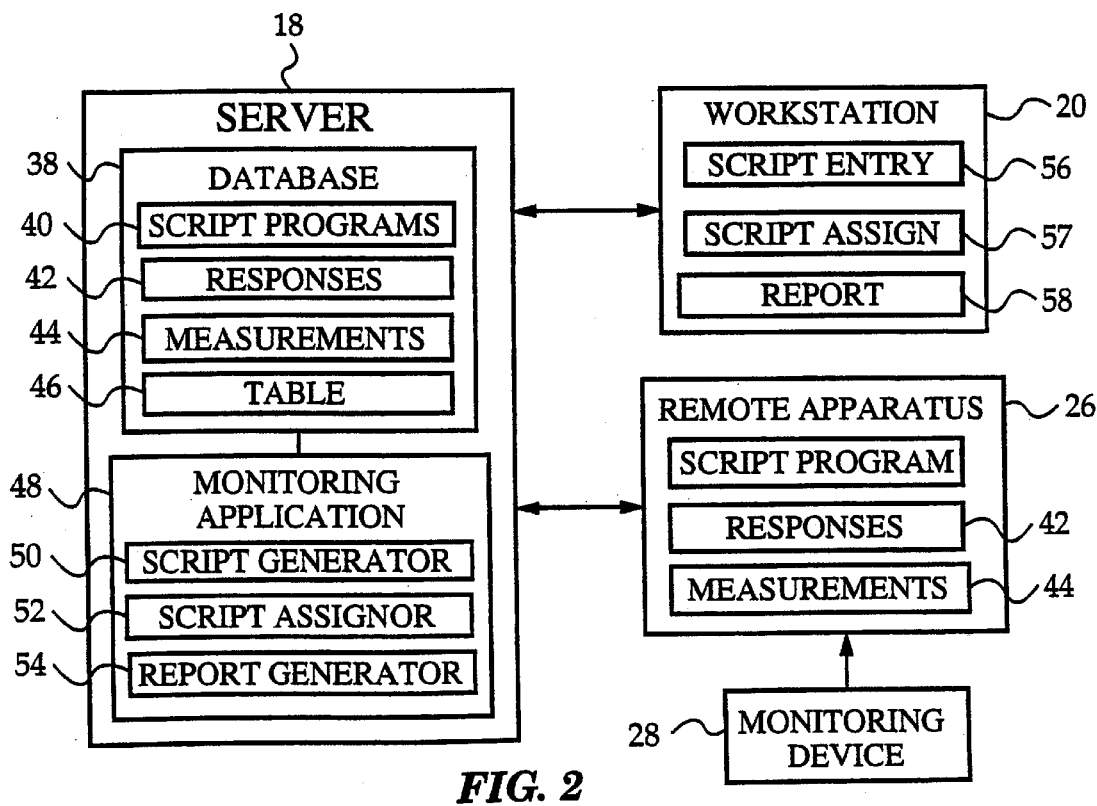
FIG. 2 is a block diagram illustrating the interaction of the components of the system of FIG. 1.

FIG. 2 shows server 18, workstation 20, and apparatus 26 in greater detail. Server 18 includes a database 38 for storing script programs 40. Script programs 40 are executed by apparatus 26 to communicate queries and messages to a patient, receive responses 42 to the queries, collect monitoring device measurements 44, and transmit responses 42 and measurements 44 to server 18. Database 38 is designed to store responses 42 and measurements 44. Database 38 further includes a look-up table 46. Table 46 contains a list of the patients and patient types to be monitored, and for each patient or patient type, a unique patient identification code and a respective pointer to the script program assigned to the patient. Each apparatus 26 is designed to execute assigned script programs 40 which it receives from server 18. As each apparatus 26 is used by a number of patients, apparatus 26 can execute any number of script programs 40.

Figure 3:
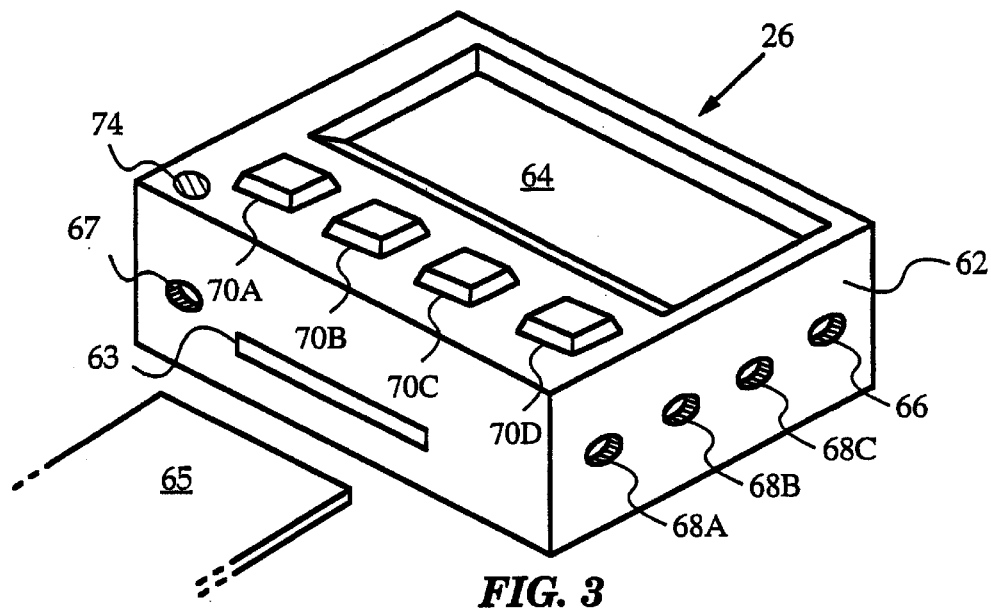
FIG. 3 is a perspective view of a remotely programmable apparatus of the system of FIG. 1.
Figure 4:
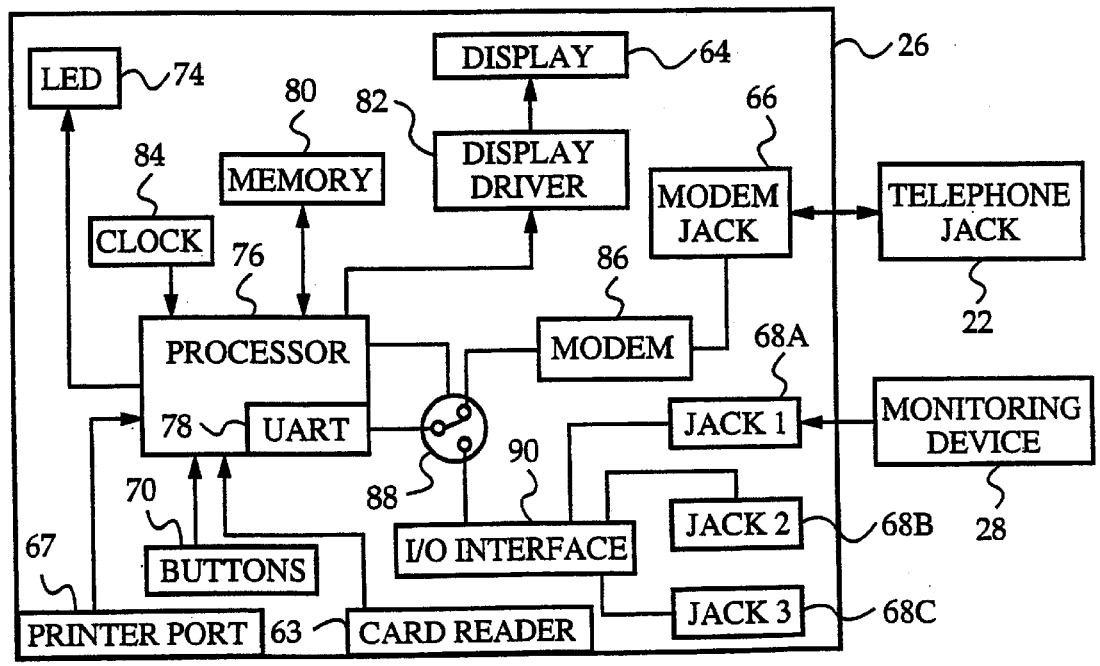
FIG. 4 is a block diagram illustrating the components of the apparatus of FIG. 3.

FIGS. 3–4 show the structure of each apparatus 26 according to the preferred embodiment. Referring to FIG. 3, apparatus 26 includes a housing 62. Housing 62 is sufficiently compact to enable apparatus 26 to be placed unobtrusively on a pharmacy counter or check stand counter. Apparatus 26 also includes a display 64 for displaying queries and prompts to the patient. In the preferred embodiment, display 64 is a liquid crystal display (LCD).

Four user input buttons 70A, 70B, 70C, and 70D are located adjacent display 64. User input buttons 70A, 70B, 70C, and 70D are for entering in apparatus 26 responses to the queries and prompts. In the preferred embodiment, user input buttons 70A, 70B, 70C, and 70D are momentary contact push buttons. In alternative embodiments, user input buttons 70A, 70B, 70C, and 70D may be replaced by switches, keys, a touch sensitive display screen, or any other data input device.

Three monitoring device jacks 68A, 68B, and 68C are located on a surface of housing 62. Device jacks 68A, 68B, and 68C are for connecting apparatus 26 to a number of monitoring devices 28, such as blood glucose meters, respiratory flow meters, or blood pressure cuffs, through respective connection cables (not shown). Apparatus 26 also includes a modem jack 66 for connecting apparatus 26 to a telephone jack through a standard connection cord (not shown). Apparatus 26 further includes a visual indicator, such as a light emitting diode (LED) 74. LED 74 is for visually notifying the patient that he or she has unanswered queries stored in apparatus 26.

Apparatus 26 also contains a data card reader 63. Data card reader 63 is capable of reading a data card 65 containing information about a patient. In the present invention, data card 65 contains the patient's identity, condition or disease, and possibly prescription information. Data card 65 is placed in data card reader 63, thus allowing apparatus 26 to identify the patient and assign script program 40. Apparatus 26 also has a printer port 67, allowing apparatus 26 to be directly connected to a printer. Queries 94, responses 42, device measurements 44, and other pertinent information stored on apparatus 26 can be printed directly.

FIG. 4 is a schematic block diagram illustrating the components of apparatus 26 in greater detail. Apparatus 26 includes a microprocessor 76, and a memory 80 connected to microprocessor 76. Memory 80 is preferably a non-volatile memory, such as a serial EEPROM. Memory 80 stores script programs 40 received from server 18, measurements 44 received from monitoring device 28, responses to queries, and a patient or patient type's unique identification code. Microprocessor 76 also includes built-in read only memory (ROM) which stores firmware for controlling the operation of apparatus 26. The firmware includes a script interpreter used by microprocessor 76 to execute script programs 40. The script interpreter interprets script commands which are executed by microprocessor 76.

The script commands allow apparatus 26 to identify the patient or patient type through user buttons 70A, 70B, 70C, and 70D, monitoring device 28, data card 65, or printer port 67. They also allow apparatus 26 to display the query sets to the patient, receive responses 42 to the query sets, receive measurements 44 from monitoring device 28, and transmit responses to server 18. Specific techniques for interpreting and executing script commands in this manner are well known in the art.

Microprocessor 76 is preferably connected to memory 80 using a standard two-wire I$^2$C interface. Microprocessor 76 is also connected to user input buttons 70A, 70B, 70C, and 70D, data card reader 63, printer port 67, LED 74, a clock 84, and a display driver 82. Clock 84 indicates the current date and time to microprocessor 76. For clarity of illustration, clock 84 is shown as a separate component, but is preferably built into microprocessor 76. Display driver 82 operates under the control of microprocessor 76 to display information on display 64. Microprocessor 76 is preferably a PIC 16C65 processor which includes a universal asynchronous receiver transmitter (UART) 78. UART 78 is for communicating with a modem 86 and a device interface 90.

A CMOS switch 88 under the control of microprocessor 76 alternately connects modem 86 and interface 90 to UART 78.

Modem 86 is connected to a telephone jack 22 through modem jack 66. Modem 86 is for exchanging data with server 18 through communication network 24. The data includes script programs 40 which are received from server 18 as well as responses 42 to queries, device measurements 44, script identification codes, and the patient or patient type's unique identification code which modem 86 transmits to server 18. Modem 86 is preferably a complete 28.8 K modem commercially available from Cermetek, although any suitable modem may be used.

Device interface 90 is connected to device jacks 68A, 68B, and 68C. Device interface 90 is for interfacing with a number of monitoring devices, such as blood glucose meters, respiratory flow meters, blood pressure cuffs, weight scales, or pulse rate monitors, through the device jacks. Device interface 90 operates under the control of microprocessor 76 to collect measurements 44 from the monitoring devices and to output the measurements to microprocessor 76 for storage in memory 80. In the preferred embodiment, device interface 90 is a standard RS 232 interface. For simplicity of illustration, only one device interface is shown in FIG. 4. However, in alternative embodiments, apparatus 26 may include multiple device interfaces to accommodate monitoring devices 28 which have different connection standards.

Referring again to FIG. 2, server 18 includes a monitoring application 48. Monitoring application 48 is a controlling software application executed by server 18 to perform the various functions described below. Application 48 includes a script generator 50, a script assignor 52, and a report generator 54. Script generator 50 is designed to generate script programs 40 from script information entered through workstation 20. The script information is entered through a script entry screen 56. In the preferred embodiment, script entry screen 56 is implemented as a web page on server 18. Workstation 20 includes a web browser for accessing the web page to enter the script information.

FIG. 5 illustrates script entry screen 56 as it appears on workstation 20. Screen 56 includes a script name field 92 for specifying the name of script program 40 to be generated. Screen 56 also includes entry fields 94 for entering query sets to be answered by a patient. Each entry field 94 has corresponding response choice fields 96 for entering response choices for the query. Screen 56 further includes check boxes 98 for selecting desired monitoring device 28, such as a blood glucose meter, respiratory flow meter, or blood pressure cuff, from which to collect measurements 44.

Screen 56 additionally includes a connection time field 100 for specifying a prescribed connection time at which apparatus 26 executing the script is to establish a subsequent communication link to server 18. The connection time is preferably selected to be the time at which communication rates are the lowest, such as 3:00 AM. During this connection time, apparatus 26 transmits to server 18 all responses 42 and device measurements 44 it has received during the day. During this same connection time, apparatus 26 also receives from server 18 all script programs 40 it will need for the following day or until the next prescribed connection time. This store and forward feature of apparatus 26 reduces communication expenses. However, if numerous patients are using apparatus 26, more than one connection can be made during the day in order to download necessary script programs 40. Screen 56 also includes a CREATE SCRIPT button 102 for instructing script generator 50 to generate script program 40 from the information entered in screen 56. Screen 56 further includes a CANCEL button 104 for canceling the information entered in screen 56.

In the preferred embodiment, each script program 40 created by the script generator 50 conforms to the standard file format used on UNIX systems. In the standard file format, each command is listed in the upper case and followed by a colon. Every line in script program 40 is terminated by a linefeed character {LF}, and only one command is placed on each line. The last character in script program 40 is a UNIX end of file character {EOF}. Table 1 shows an exemplary listing of script commands used in the preferred embodiment of the invention.

Script program 40 further includes a collect command to collect device measurements 44 from monitoring device 28 specified in check boxes 98. Script program 40 also includes commands to establish a subsequent communication link to server 18 at the connection time specified in field 100. The steps included in script program 40 are also shown in the flow chart of FIGS. 12A–12B and will be discussed in the operation section below.

Referring again to FIG. 2, script assignor 52 is for assigning script programs 40 to the patients. Script programs 40 are assigned in accordance with script assignment information entered through workstation 20. The script assignment information is entered through a script assignment screen 57, which is preferably implemented as a web page on server 18.

TABLE 1

SCRIPT COMMANDS

| Command | Description |
| --- | --- |
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars} {LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t {LF} | Wait until time t specified in the DELAY command, usually the prescribed connection time. |
| CONNECT: {LF} | Perform a connection routine to establish a communication link to the server, transmit the patient or patient type identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art that many other suitable scripting languages and sets of script commands may be used to implement the invention.

Script generator 50 preferably stores a script program template which it uses to create each script program 40. To generate script program 40, script generator 50 inserts into the template the script information entered in screen 56. For example, FIGS. 6A–6B illustrate sample script program 40 created by script generator 50 from the script information shown in FIG. 5.

Script program 40 includes identification commands to determine the patient or patient type from user buttons 70A, 70B, 70C, and 70D, monitoring device 68A, 68B, and 68C, card chip reader 64, printer port 67, and display commands to display the queries and response choices entered in fields 94 and 96, respectively. Script program 40 also includes input commands to receive responses 42 to the queries.

FIG. 7 illustrates a sample script assignment screen 57 as it appears on workstation 20. Screen 57 includes check boxes 106 for selecting script program 40 to be assigned and check boxes 108 for selecting the patient or patient types to whom script program 40 is to be assigned. Screen 57 also includes an ASSIGN SCRIPT button 112 for entering the assignments. When button 112 is pressed, script assignor 52 creates and stores for each patient or patient type selected in check boxes 108 a respective pointer to script program 40 selected in check boxes 106. Each pointer is stored in the patient or patient type look-up table 46 of database 38. Screen 57 further includes an ADD SCRIPT button 110 for accessing script entry screen 56 and a DELETE SCRIPT button 114 for deleting script program 40.

Referring again to FIG. 2, report generator 54 is designed to generate a patient report 58 from the responses and device measurements received in server 18. Patient report 58 is displayed on workstation 20. FIG. 10 shows a sample patient report 58 produced by report generator 54 for a selected patient. Patient report 58 includes a graph 116 of device measurements 44 received from the patient, as well as a listing of responses 42 received from the patient. Specific techniques for writing a report generator program to display data in this manner are well known in the art.

Figure 11A:
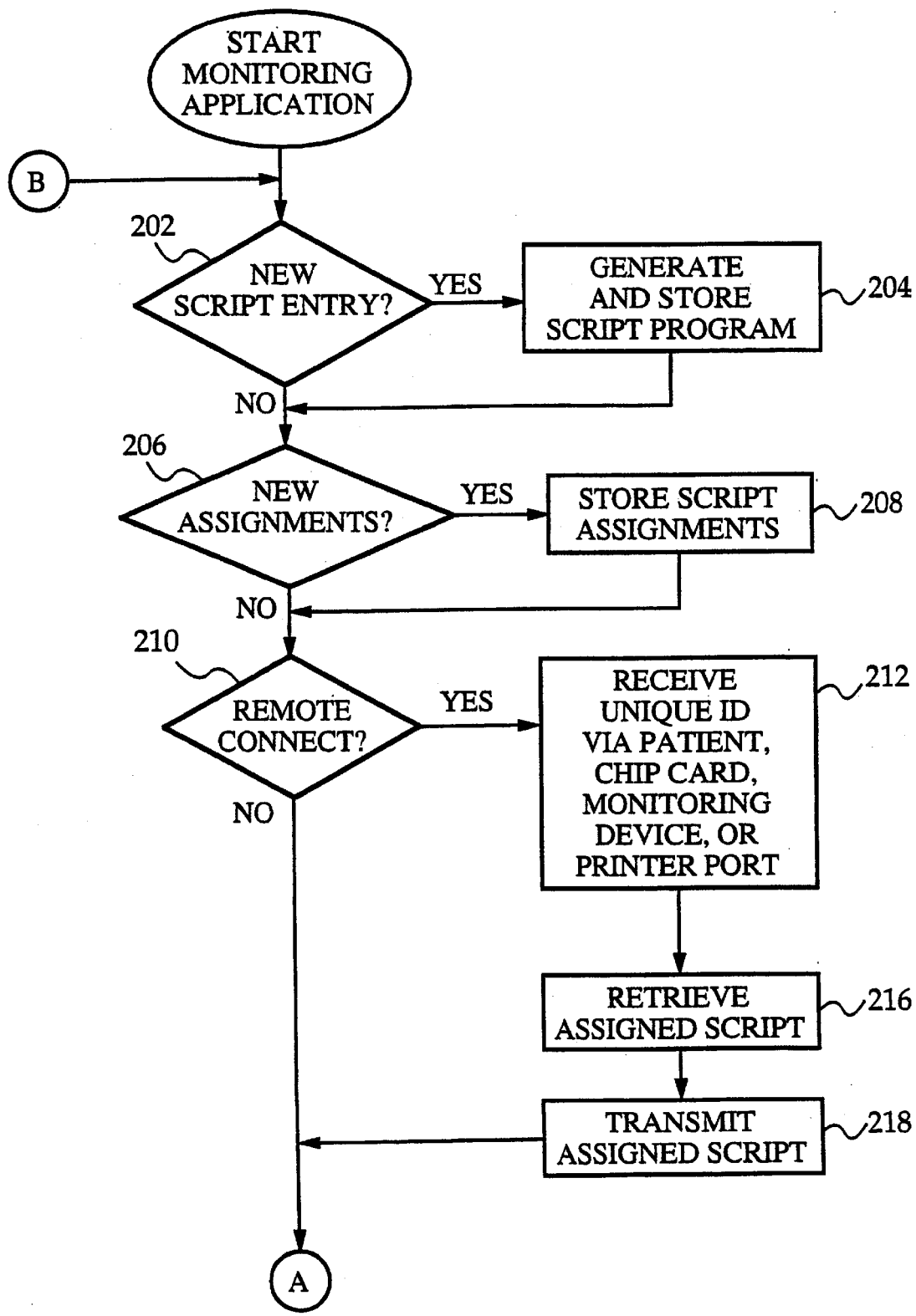
FIG. 11A is a flow chart illustrating the steps included in a monitoring application executed by the server of FIG. 1 according to the preferred embodiment of the invention.
Figure 11B:
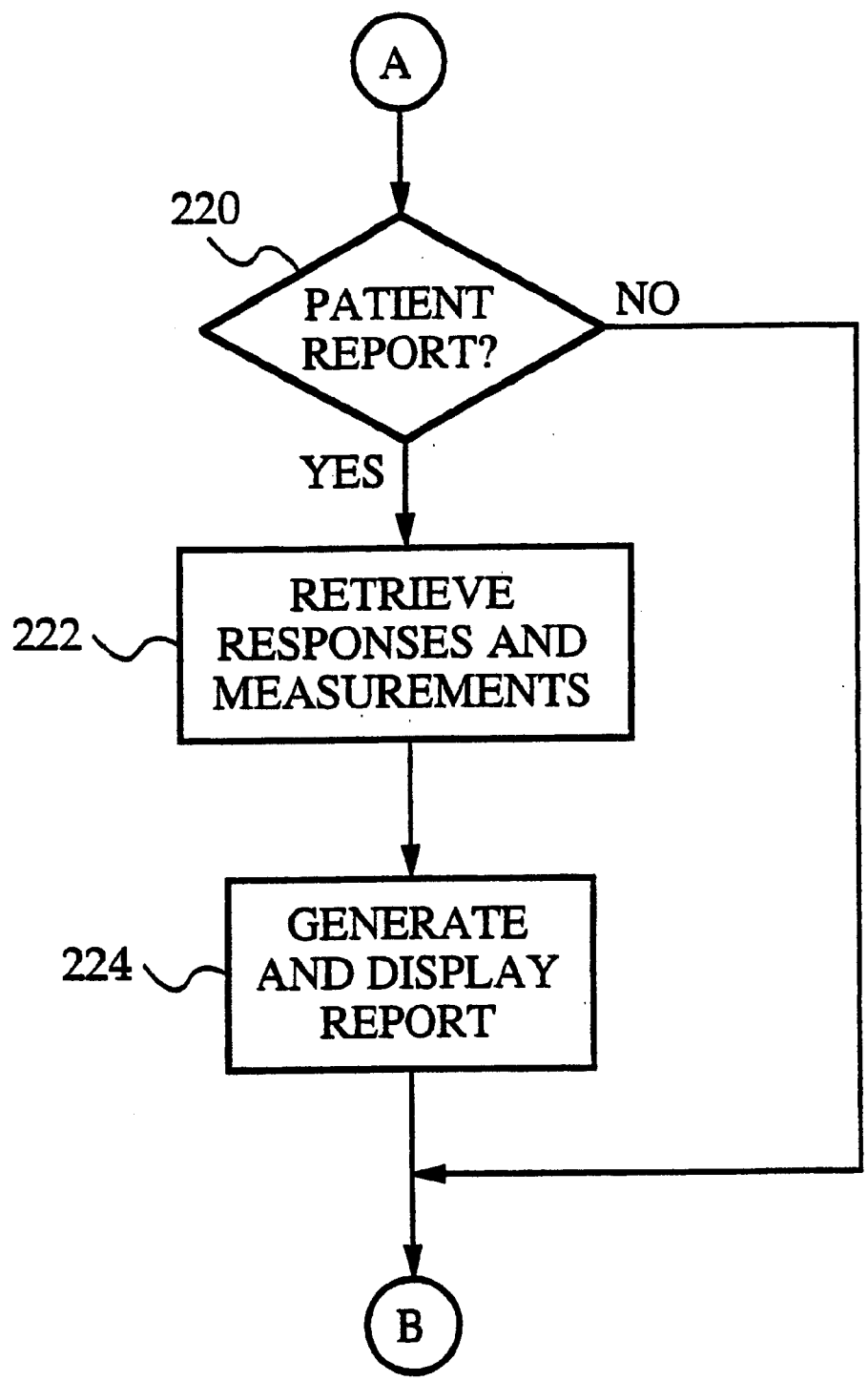
FIG. 11B is a continuation of the flow chart of FIG. 11A.

The operation of the preferred embodiment is illustrated in FIGS. 11A and 11B. FIG. 11A is a flow chart illustrating steps included in the monitoring application executed by server 18. FIG. 11B is a continuation of the flow chart of FIG. 11A. In step 202, server 18 determines if new script information has been entered through script entry screen 56. If new script information has not been entered, server 18 proceeds to step 206. If new script information has been entered, server 18 proceeds to step 204.

As shown in FIG. 5, the script information includes queries 94, and for each query 94, corresponding responses choices 96. The script information also includes a selected monitoring device type from which to collect device measurements 44. The script information further includes a prescribed connection time for each apparatus to establish a subsequent communication link to server 18. The script information is generally entered in server 18 by a healthcare provider, such as the patients' physician or case manager. Of course, any person desiring to communicate with the patients may also be granted access to server 18 to create and assign script programs 40. Further, it is to be understood that the system may include any number of workstations 20 for entering script generation and script assignment information in server 18.

In step 204, script generator 50 generates script program 40 from the information entered in screen 56. Script program 40 is stored in database 38. Steps 202 and 204 are preferably repeated to generate multiple script programs, e.g. a script program for diabetes patients, a script program for asthma patients, etc. Each script program 40 corresponds to a respective one of the sets of queries 94 entered through script entry screen 56. Following step 204, server 18 proceeds to step 206.

In step 206, server 18 determines if new script assignment information has been entered through assignment screen 57. If new script assignment information has not been entered, server 18 proceeds to step 210. If new script assignment information has been entered, server 18 proceeds to step 208. As shown in FIG. 7, script programs 40 are assigned to each patient by selecting script program 40 through check boxes 106, selecting the patient or patient types to whom selected script program 40 is to be assigned through check boxes 108, and pressing the ASSIGN SCRIPT button 112. When button 112 is pressed, script assignor 52 creates for each patient or patient type selected in check boxes 108 a respective pointer to script program 40 selected in check boxes 106. In step 208, each pointer is stored in look-up table 46 of database 38. Following step 208, server 18 proceeds to step 210.

In step 210, server 18 determines if apparatus 26 is remotely connected to server 18. If not, server 18 proceeds directly to step 220. If apparatus 26 is connected, server 18 receives from apparatus 26 the patient or patient type's unique identification code in step 212. This step can be achieved in a number of ways. The patient can answer specific queries on display 64 of apparatus 26, which allows identification of the patient's identity, condition, or disease. The patient's identification can also be recognized via monitoring device 28. Monitoring device 28 can contain the patient's unique identification code, and can send it to apparatus 26. Apparatus 26 is also capable of recognizing the type of monitoring device 28, for example a blood glucose meter, to determine the patient type, for example diabetes.

Data card reader 63 is a third way in which apparatus 26 can recognize a patient or patient type. Data card 65 contains information about the patient's identity, condition or disease, and possibly prescription information, which can be read by data card reader 63 of apparatus 26. This information is then sent to server 18, where it is used to determine which script program 40 is sent back to apparatus 26 to which the patient is to respond.

Figure 20:
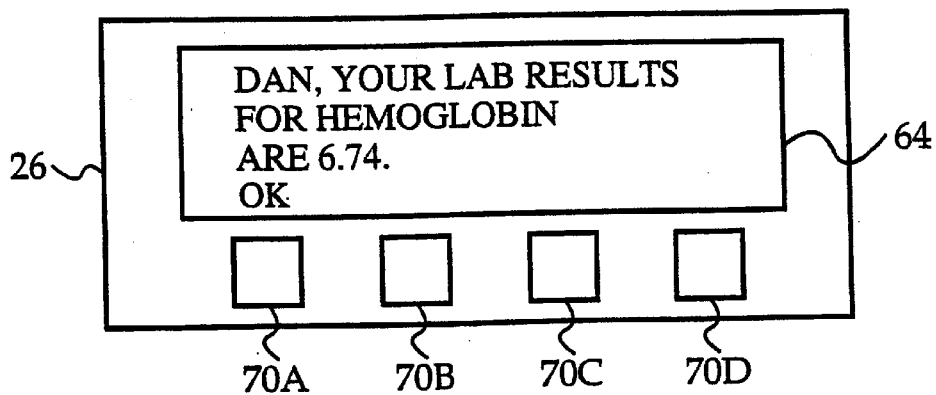
FIG. 20 is a second sample message, appearing on the display of the apparatus of FIG. 3.
Figure 21:
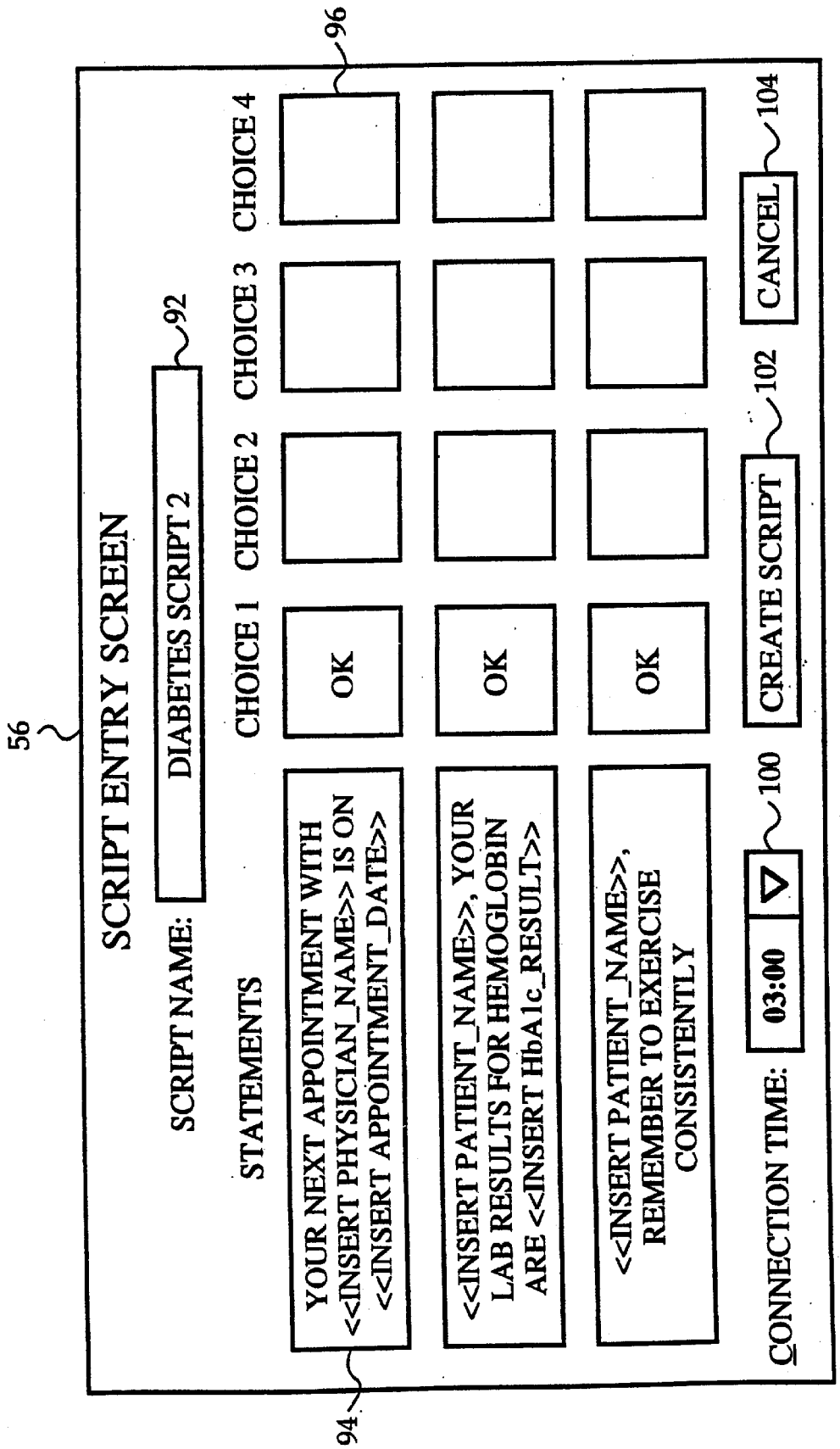
FIG. 21 is a script entry screen according to the third embodiment of the invention.

A fourth way in which apparatus 26 can identify a patient or patient type is through printer port 67, as illustrated in FIG. 20. Patient data from the server 106 of another information system can be sent to a printer 108 via apparatus 26. Apparatus 26 can then send the intercepted data to server 18 of the remote monitoring system of the present invention, which can then send appropriate script program 40 to apparatus 26. A more detailed description of the data interception embodiment of the present invention is described below.

In step 216, server 18 uses the patient identification code to retrieve from table 46 the pointer to script program 40 assigned to the patient. Server 18 then retrieves assigned script program 40 from database 38. In step 218, server 18 transmits assigned script program 40 to patient's apparatus 26 through communication network 24. Following step 218, server 18 proceeds to step 220.

In step 220, server 18 determines if a patient report request has been received from workstation 20. If no report request has been received, server 18 returns to step 202. If a report request has been received for a selected patient, server 18 retrieves from database 38, measurements 44 and query responses 42 last received from the patient, step 222. In step 224, server 18 generates and displays patient report 58 on workstation 20. As shown in FIG. 10, report 58 includes device measurements 44 and query responses 42 last received from the patient. Following step 224, the server returns to step 202.

Figure 12A:
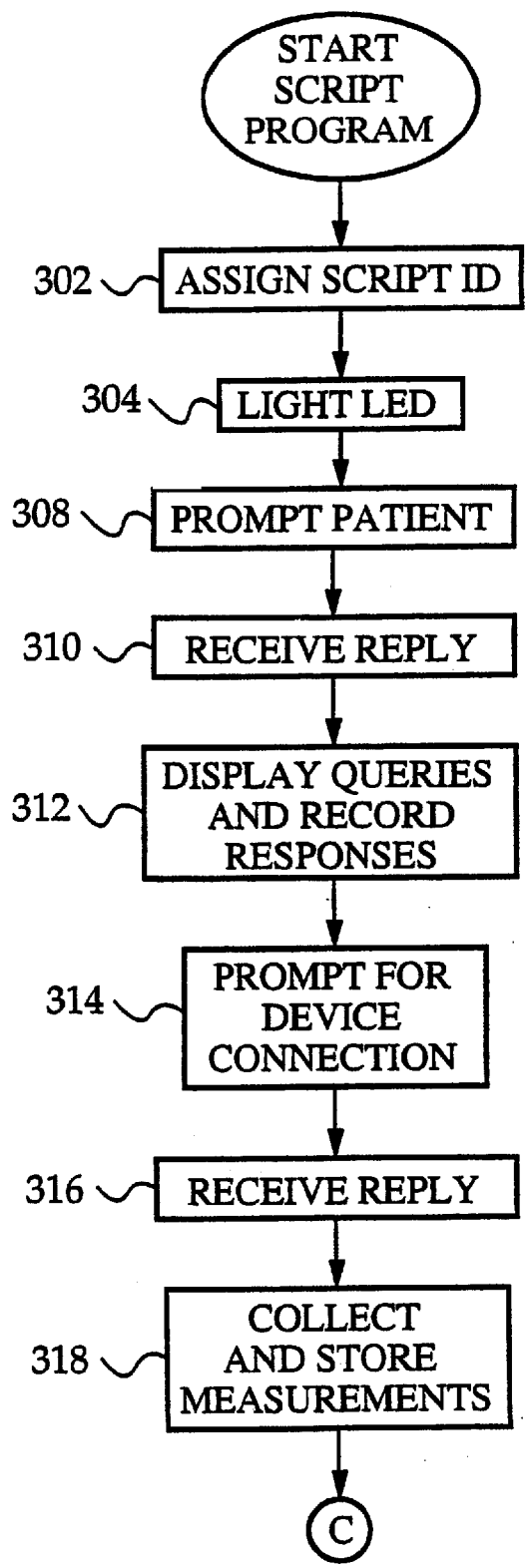
FIG. 12A is a flow chart illustrating the steps included in the script program of FIGS. 6A–6B.
Figure 12B:
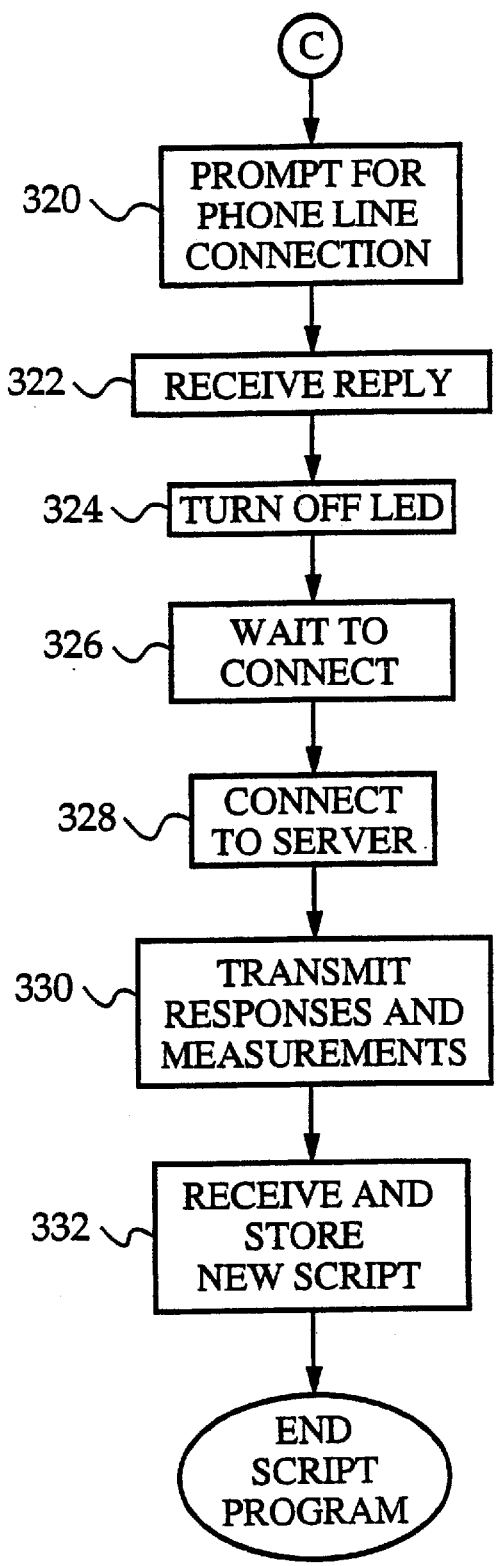
FIG. 12B is a continuation of the flow chart of FIG. 12A.

FIGS. 12A–12B illustrate the steps included in script program 40 executed by apparatus 26. Before script program 40 is received, apparatus 26 receives the patient or patient type's unique identification code, and is programmed with the script interpreter used by microprocessor 76 to execute script program 40. The initial programming may be achieved during the connection to server 18. Following initial programming, apparatus 26 receives from server 18 script program 40 assigned to the patient associated with apparatus 26. Script program 40 is received by modem 86 through a first communication link and stored in memory 80.

In step 302, microprocessor 76 assigns a script identification code to script program 40 and stores the script identification code in memory 80. In step 304, microprocessor 76 lights LED 74 to notify the patient that he or she has unanswered queries stored in apparatus 26. LED 74 preferably remains lit until the queries are answered by the patient.

In step 308, microprocessor 76 prompts the patient by displaying on display 64 "ANSWER QUERIES NOW? PRESS ANY BUTTON TO START". In step 310, microprocessor 76 waits until a reply to the prompt is received from the patient. When a reply is received, microprocessor 76 proceeds to step 312. In step 312, microprocessor 76 executes successive display and input commands to display the queries and response choices on display 64 and to receive responses 42 to the queries.

FIG. 8 illustrate a sample query and its corresponding response choices as they appear on display 64. The response choices are positioned on display 64 such that each response choice is located proximate to a respective one of input buttons 70A, 70B, 70C, and 70D. In the preferred embodiment, each response choice is displayed immediately above respective input button 70. The patient presses input button 70A, 70B, 70C, and 70D corresponding to his or her response. Microprocessor 76 stores each response in memory 80.

In steps 314–318, microprocessor 76 executes commands to collect device measurements 44 from selected monitoring device 28 if it is directed to do so by script program 40. Script program 40 specifies selected monitoring device 28 from which to collect measurements 44. In step 314, microprocessor 76 prompts the patient to connect selected monitoring device 28, for example a blood glucose meter, to one of device jacks 68A, 68B, and 68C. A sample prompt is shown in FIG. 10. In step 316, microprocessor 76 waits until a reply to the prompt is received from the patient. When a reply is received, microprocessor 76 proceeds to step 318. Microprocessor 76 also connect s UART 78 to interface 90 through switch 88. In step 318, microprocessor 76 collects device measurements 44 from monitoring device 28 through interface 90. Measurements 44 are stored in memory 80.

In the preferred embodiment, apparatus 26 is always plugged into telephone jack 22. If not, however, microprocessor 76 prompts the patient to connect apparatus 26 to telephone jack 22 so that apparatus 26 may connect to server 18 at the prescribed connection time in step 320. In step 322, microprocessor 76 waits until a reply to the prompt is received from the patient. When a reply is received, microprocessor 76 turns off LED 74 in step 324. In step 326, microprocessor 76 waits until it is time to connect to server 18. Microprocessor 76 compares the connection time specified in script program 40 to the current time output by clock 84. When it is time to connect, microprocessor 76 connects UART 78 to modem 86 through switch 88.

In step 328, microprocessor 76 establishes a subsequent communication link between apparatus 26 and server 18 through modem 86 and communication network 24. If the connection fails for any reason, microprocessor 76 repeats step 328 to get a successful connection. In step 330, microprocessor 76 transmits device measurements 44, query responses 42, script identification code, and patient or patient type identification code stored in memory 80 to server 18 through the subsequent communication link. In step 332, microprocessor 76 receives through modem 86 new script program 40 from server 18. New script program 40 is stored in memory 80 for subsequent execution by microprocessor 76. Following step 332, script program 40 ends.

Figure 13:
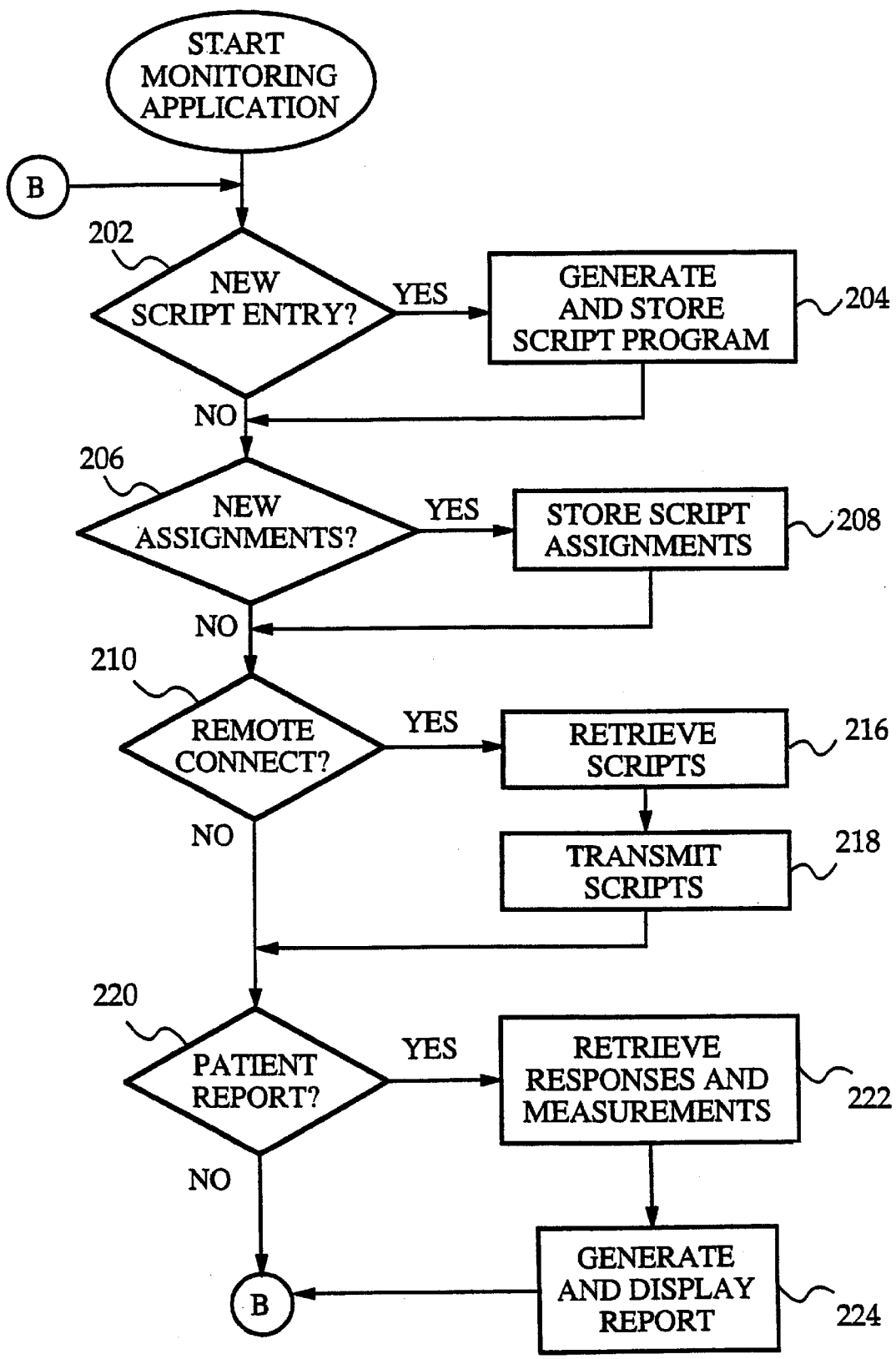
FIG. 13 flow chart illustrating the steps included in a monitoring application executed by the server of FIG. 1 according to an alternative embodiment of the invention.

In the above description, apparatus 26 connects to server 18 each time a new patient identification is entered. FIG. 13 shows an alternative embodiment, where apparatus 26 connects to server 18 at one time during the day. During this connection period, apparatus 26 receives from server 18 all script programs 40 it expects to need during the following day. As shown in FIG. 13, steps 202–208 are the same as above, with server 18 generating and storing new script assignments and new script programs if needed. In step 210, apparatus 26 connects with server 18. In step 216, server 18 retrieves script programs 40 from database 38. Script programs 40 can be for patients who are likely to use apparatus 26 the following day, or script programs 40 can be for general conditions, diseases, or prescriptions that are requested everyday. In step 218, server 18 transmits assigned script program 40 to patient's apparatus 26 through communication network 24. Following step 218, server 18 proceeds to step 220, which is carried out in the same manner as the embodiment illustrated in FIGS. 11A and 11B.

Figure 14A:
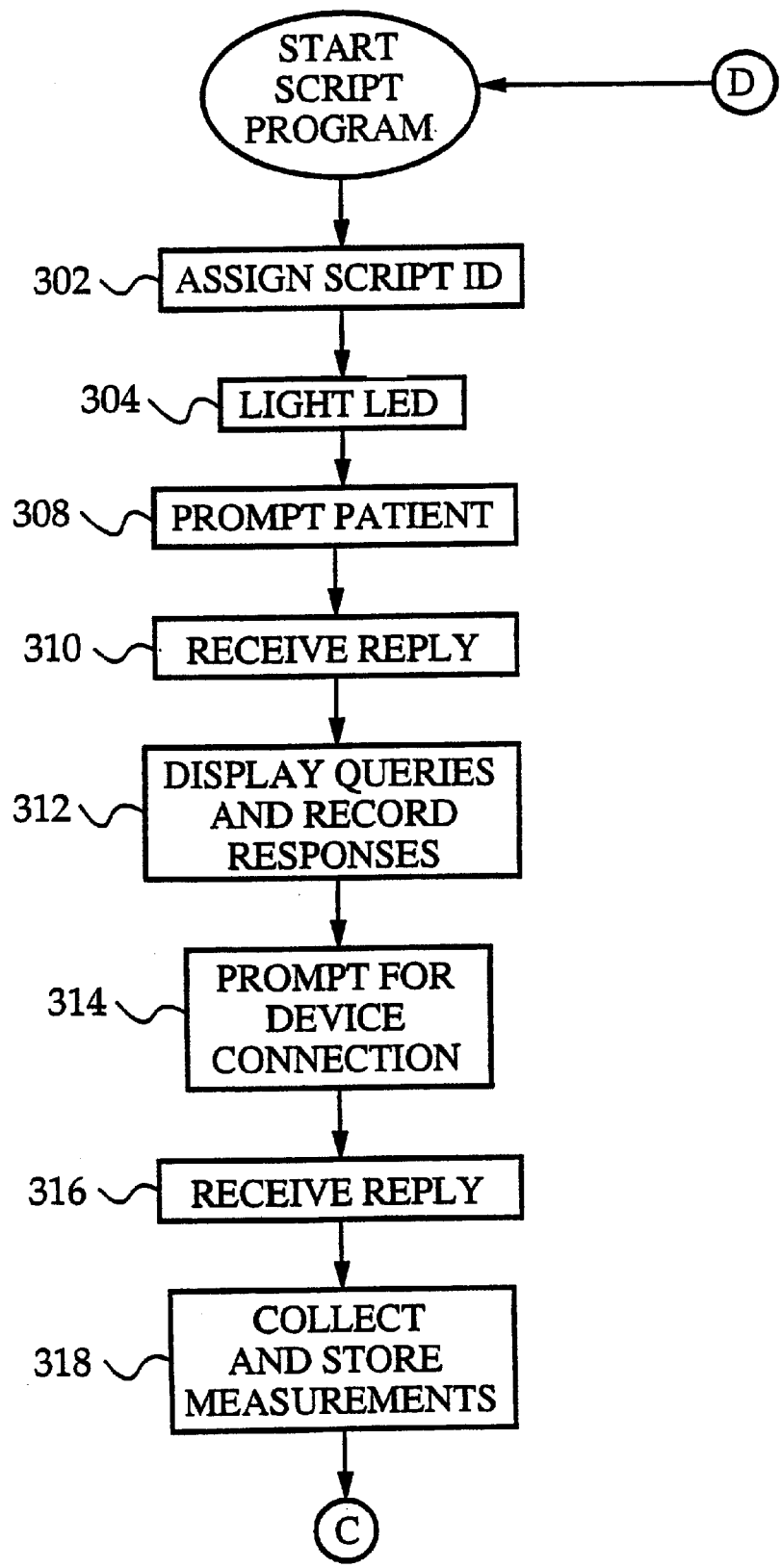
FIG. 14A is a flow chart illustrating the steps included in the script program used in the alternative embodiment of the invention.
Figure 14B:
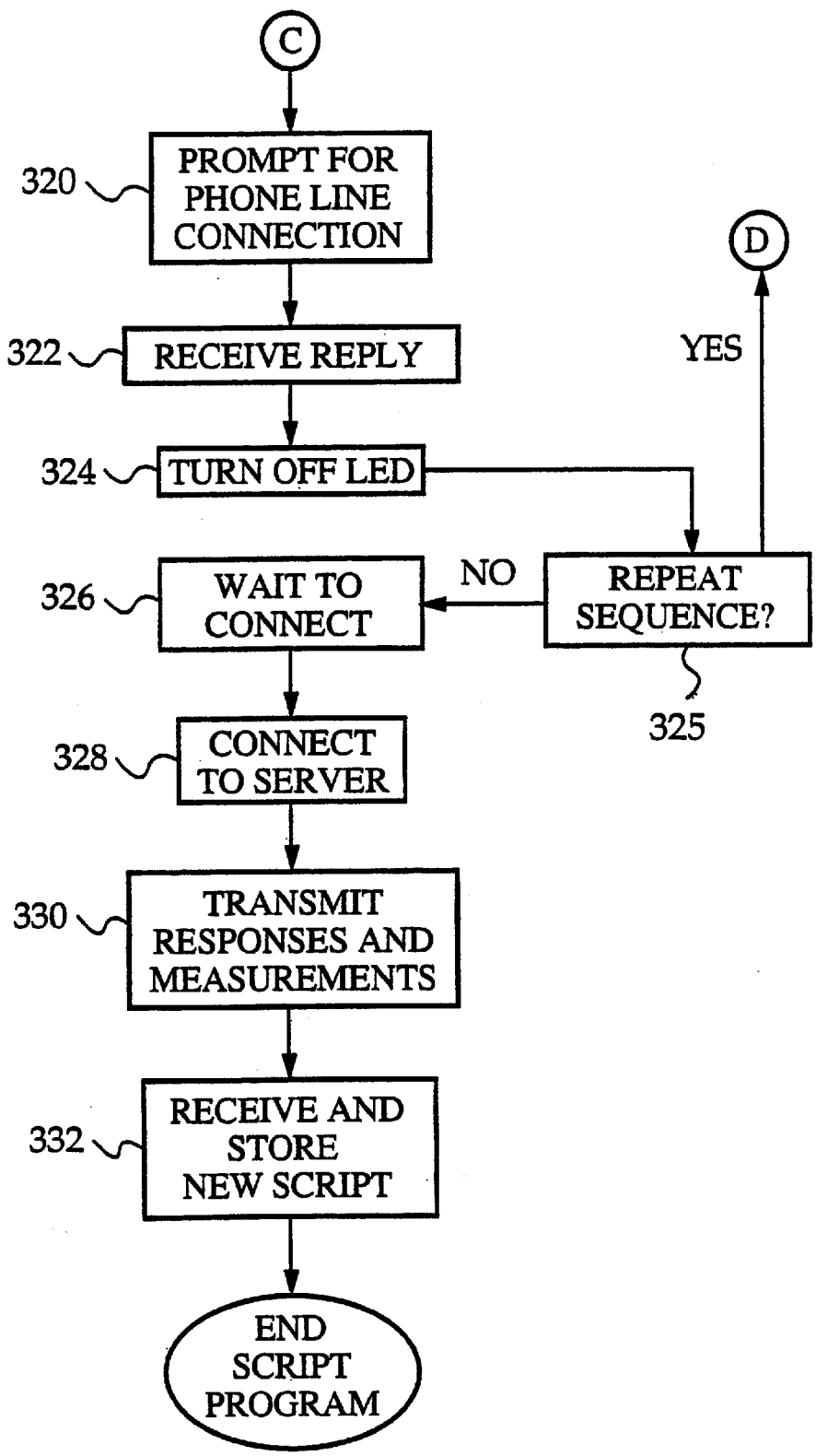
FIG. 14B is a continuation of the flow chart of FIG. 14A.
Figure 15:
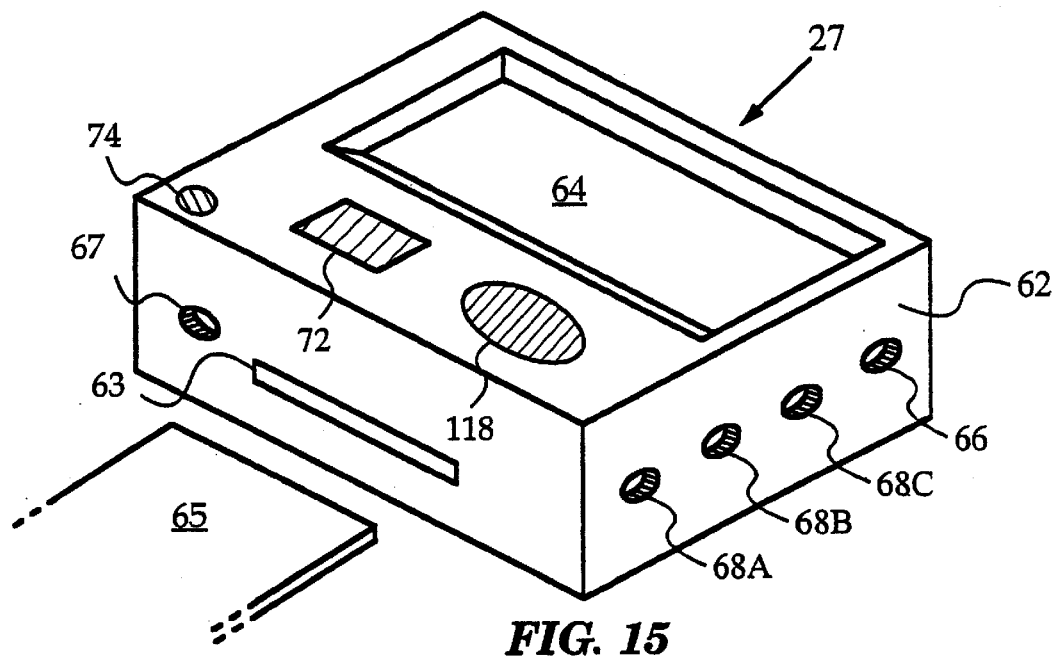
FIG. 15 is a perspective view of a remotely programmable apparatus according to a second embodiment of the invention.

In the embodiment of FIG. 13, patients' responses to all queries are transmitted from apparatus 26 to server 18 during a single connection period, ideally the same connection period when script programs 40 are downloaded into apparatus 26 for the following day. FIGS. 14A and 14B show the steps of script program 40 for the embodiment of FIG. 13. Notice all steps are the same, except for the addition of step 325. In step 325, apparatus 26 has the option of repeating another script program sequence for the same or another patient before connecting to server 18. Thus, many patients can use apparatus 26 during the day. Apparatus 26 stores all their responses 42 and measurements 44, and then forwards them to server 18 at the end of the day, as shown in step 330. Apparatus 26 used in this embodiment must have sufficient memory means 80.

The main advantage of the present invention is that it does not require that each patient purchase his or her own apparatus 26. Instead, patients can visit their nearest pharmacy or healthcare clinic where apparatus 26 is located and answer queries there. Since apparatus 26 only requires identification of a patient or patient type in order to connect to server 18 and download appropriate script program 40, any patient can use any apparatus 18 as long as they have a patient identification code, data card, or monitoring device. Ideally, patients who are traveling or are far from home can just stop into any pharmacy and answer queries, which will get sent back to server 18.

A second advantage of the monitoring system is that it allows each apparatus 26 to be programmed remotely through script programs 40. Patient surveys, connection times, display prompts, selected monitoring devices, patient customization, and other operational details of each apparatus may be easily changed by transmitting a new script program 40 to apparatus 26. Moreover, each script program 40 may be easily created and assigned by remotely accessing server through 18 the Internet. Thus, the invention provides a powerful, convenient, and inexpensive system for remotely monitoring a large number of patients.

Figure 16:
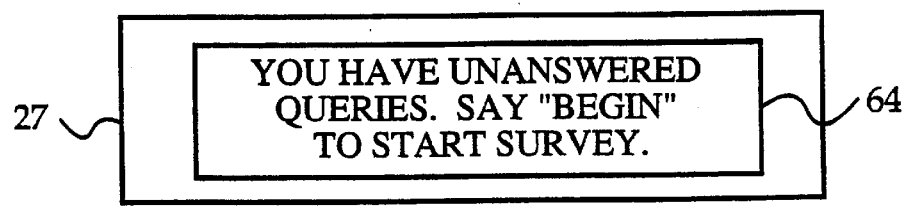
FIG. 16 is a sample prompt appearing on a display of the apparatus of FIG. 15.
Figure 17:
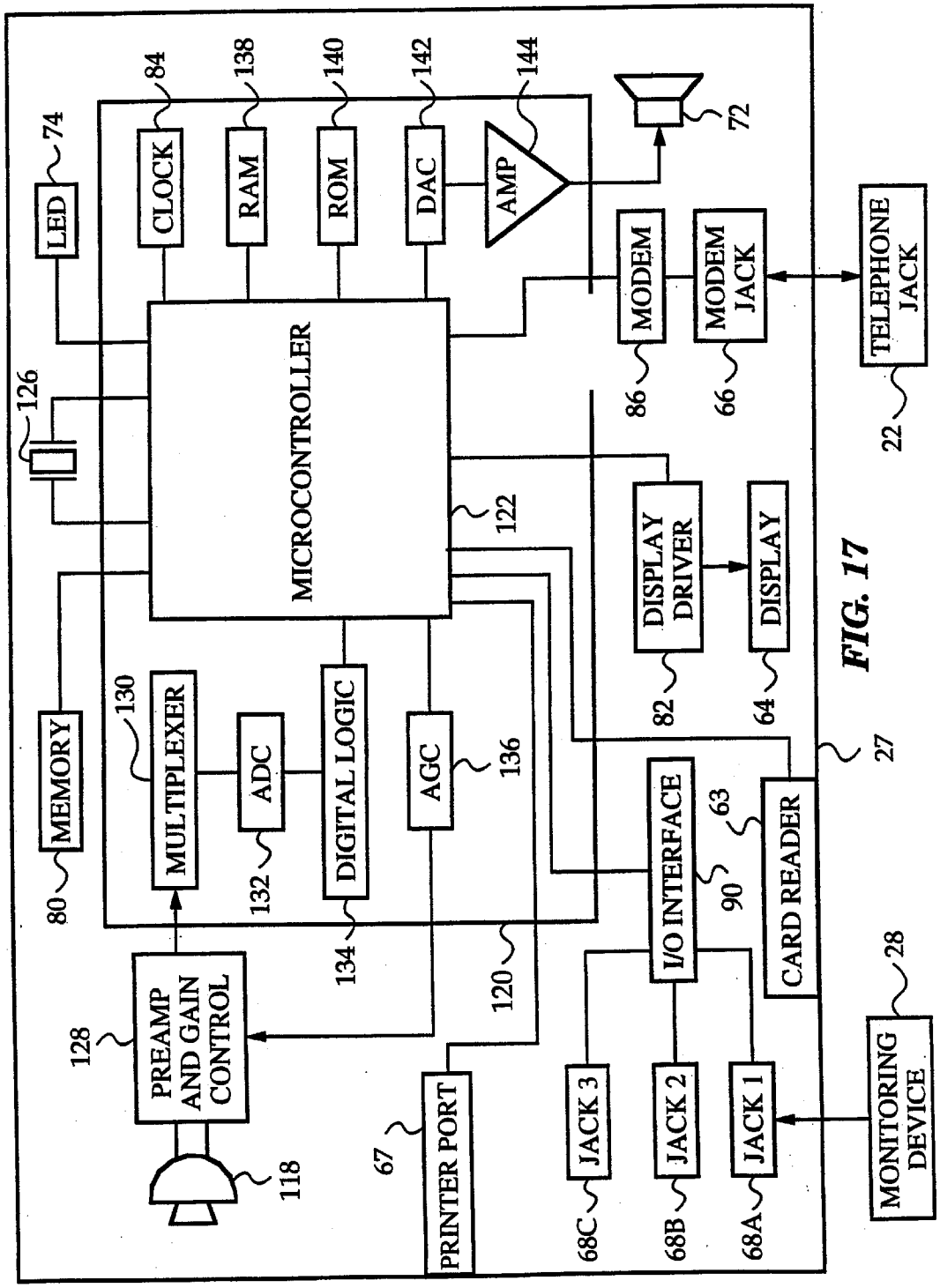
FIG. 17 is a block diagram illustrating the components of the apparatus of FIG. 15.
Figure 18:
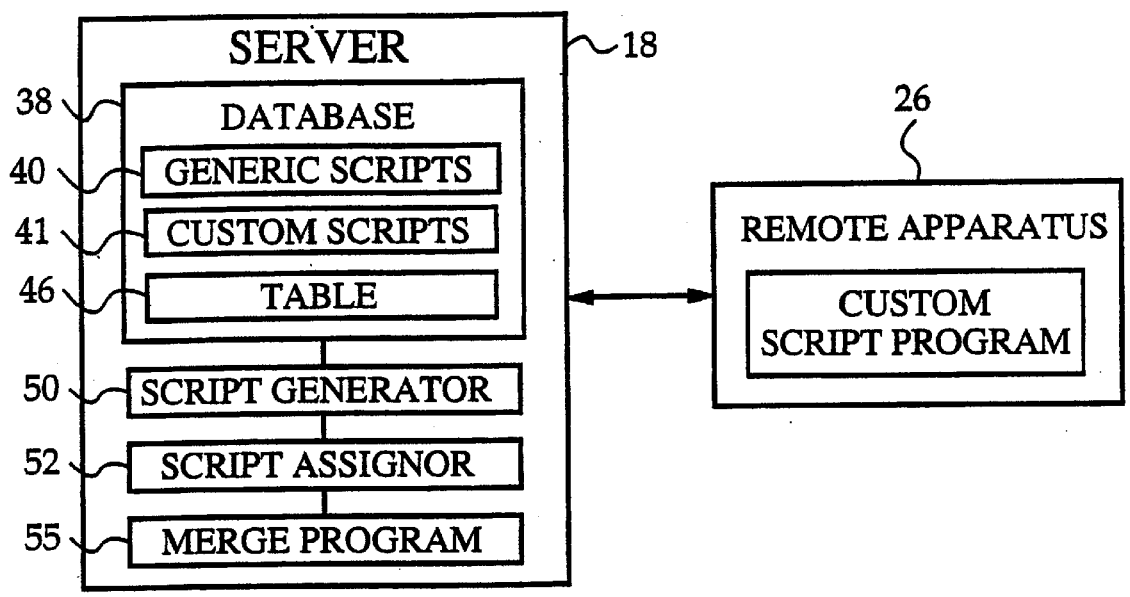
FIG. 18 is a schematic block diagram illustrating the interaction of the server of FIG. 1 with the apparatus of FIG. 3 according to a third embodiment of the invention.

FIGS. 16–18 illustrate a second embodiment of the invention in which each remotely programmable apparatus has speech recognition and speech synthesis functionality. FIG. 14 shows a perspective view of an apparatus 27 according to the second embodiment. Apparatus 27 includes a speaker 72 for audibly communicating queries and prompts to the patient. Apparatus 27 also includes a microphone 118 for receiving spoken responses to the queries and prompts. Apparatus 27 may optionally include a display 64 for displaying prompts to the patient, as shown in FIG. 17.

FIG. 18 is a schematic block diagram illustrating the components of apparatus 27 in greater detail. Apparatus 27 is similar in design to apparatus 26 of the preferred embodiment except that apparatus 27 includes an audio processor chip 120 in place of microprocessor 76. Audio processor chip 120 is preferably an RSC-164 chip commercially available from Sensory Circuits Inc. of 1735 N. First Street, San Jose, Calif. 5112.

Audio processor chip 120 has a microcontroller 122 for executing script programs 40 received from server 18. A memory 80 is connected to microcontroller 122. Memory 80 stores script programs 40 and a script interpreter used by microcontroller 122 to execute script programs 40. Memory 80 also stores measurements 44 received from monitoring device 28, responses 42 to the queries, and script identification codes.

Audio processor chip 120 also has built in speech synthesis functionality for synthesizing queries and prompts to a patient through speaker 72. For speech synthesis, chip 120 includes a digital to analog converter (DAC) 142 and an amplifier 144. DAC 142 and amplifier 144 drive speaker 72 under the control of microcontroller 122.

Audio processor chip 120 further has built in speech recognition functionality for recognizing responses spoken into microphone 118. Audio signals received through microphone 118 are converted to electrical signals and sent to a preamp and gain control circuit 128. Preamp and gain control circuit 128 is controlled by an automatic gain control circuit 136, which is in turn controlled by microcontroller 122. After being amplified by preamp 128, the electrical signals enter chip 120 and pass through a multiplexer 130 and an analog to digital converter (ADC) 132. The resulting digital signals pass through a digital logic circuit 134 and enter microcontroller 122 for speech recognition.

Audio processor chip 120 also includes a RAM 138 for short term memory storage and a ROM 140 which stores programs executed by microcontroller 122 to perform speech recognition and speech synthesis. Chip 120 operates at a clock speed determined by a crystal 126. Chip 120 also includes a clock 84 which provides the current date and time to microcontroller 122. As in the preferred embodiment, apparatus 27 includes an LED 74, display driver 82, modem 86, and device interface 90, all of which are connected to microcontroller 122.

The operation of the second embodiment is similar to the operation of the preferred embodiment except that queries, response choices, and prompts are audibly communicated to the patient through speaker 72 rather than being displayed to the patient on display 64. The operation of the second embodiment also differs from the operation of the preferred embodiment in that responses 42 to the queries and prompts are received through microphone 118 rather than through user input buttons.

Script programs 40 of the second embodiment are similar to the script program shown in FIGS. 6A–6B, except that each display command is replaced by a speech synthesis command and each input command is replaced by a speech recognition command. The speech synthesis commands are executed by microcontroller 122 to synthesize queries, response choices, and prompts through speaker 72. The speech recognition commands are executed by microcontroller 122 to recognize responses 42 spoken into microphone 118.

For example, to ask the patient how he or she feels and record a response, microcontroller 122 first executes a speech synthesis command to synthesize through speaker 72 "How do you feel? Please answer with one of the following responses: very bad, bad, good, or very good." Next, microcontroller 118 executes a speech recognition command to recognize the response spoken into microphone 118. The recognized response is stored in memory 80 and subsequently transmitted to server 18. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 18–21 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

The third embodiment also shows how the queries and statements may be customized to each individual by merging personal data with the script programs, much like a standard mail merge application. Referring to FIG. 18, personal data relating to each individual is preferably stored in look-up table 46 of database 38. By way of example, the data may include each individual's name, the name of each individual's physician, test results, appointment dates, or any other desired data. As in the preferred embodiment, database 38 also stores generic script programs 40 created by script generator 50.

Figure 19:
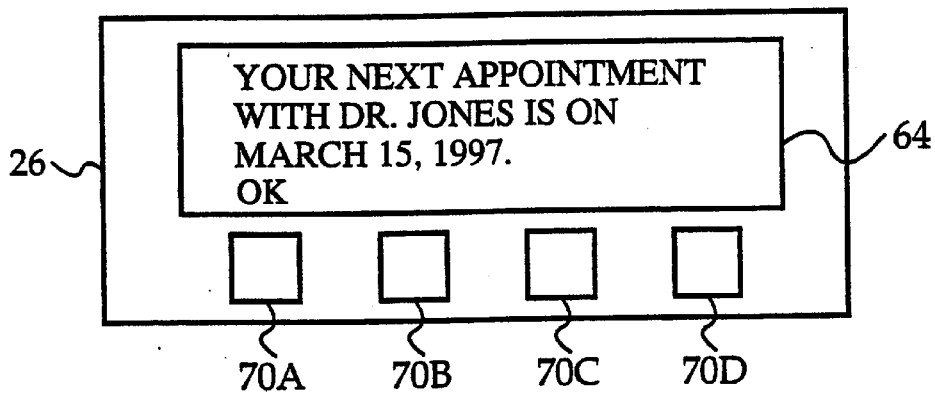
FIG. 19 is a first sample message, appearing on the display of the apparatus of FIG. 3.

Server 18 includes a data merge program 55 for merging the data stored in table 46 with generic script programs 40. Data merge program 55 is designed to retrieve selected data from table 46 and to insert the data into statements in generic script programs 40, thus creating custom script programs 41. Each custom script program 41 contains statements which are customized to an individual. For example, the statements may be customized with the individual's name, test results, etc. Examples of such customized statements are shown in FIGS. 19 and 20.

The operation of the third embodiment is similar to the operation of the preferred embodiment except that script programs 40 are used to communicate messages to the individuals rather than to query the individuals. Each message is preferably a set of statements. Referring to FIG. 18, the statements may be entered in server 18 through script entry screen 56, just like the queries of the preferred embodiment.

Each statement preferably includes one or more insert commands specifying data from table 46 to be inserted into the statement. The insert commands instruct data merge program 55 to retrieve the specified data from database 38 and to insert the data into the statement. For example, the insert commands shown in FIG. 21 instruct the data merge program to insert a physician name, an appointment date, a patient name, and a test result into the statements. As in the preferred embodiment, each statement may also include one or more response choices which are entered in fields 96.

Following entry of the statements and response choices, CREATE SCRIPT button 102 is pressed. When button 102 is pressed, script generator 50 generates a generic script program from the information entered in screen 56. The generic script program is similar to script program 40 shown in FIGS. 6A–6B, except that the display commands specify statements to be displayed rather than queries. Further, the statements include insert commands specifying data to be inserted into script program 40. As in the preferred embodiment, multiple script programs are preferably generated, e.g. a generic script program for diabetes patients, a generic script program for asthma patients, etc. The generic script programs are stored in database 38.

Following generation of the generic script programs, server 18 receives script assignment information entered through script assignment screen 57. As shown in FIG. 7, script programs 40 are assigned by first selecting one of the generic script programs through check boxes 106, selecting individuals through check boxes 108, and pressing the ASSIGN SCRIPT button 112. When button 112 is pressed, data merge program 55 creates a custom script program for each individual selected in check boxes 108.

Each custom script program is preferably created by using the selected generic script program as a template. For each individual selected, data merge program 55 retrieves from database 38 the data specified in the insert commands. Next, data merge program 55 inserts the data into the appropriate statements in the generic script program to create a custom script program for the individual. Each custom script program is stored in database 38.

As each custom script program is generated for an individual, script assignor 52 assigns the custom script program to the individual. This is preferably accomplished by creating a pointer to the custom script program and storing the pointer with the individual's unique identification code in table 46. When the individual's remote apparatus connects to server 18, server 18 receives from apparatus 26 the individual's unique identification code. Server 18 uses the unique identification code to retrieve from table 46 the pointer to the custom script program assigned to the individual. Next, server 18 retrieves the assigned custom script program from database 38 and transmits the assigned custom script program to apparatus 26 through communication network 24.

Apparatus 26 receives and executes script program 40. The execution of script program 40 is similar to the execution described in the preferred embodiment, except that statements are displayed to the individual rather than queries. FIGS. 17–18 illustrate two sample statements as they appear on display 64. Each statement includes a response choice, preferably an acknowledgment such as "OK". After reading a statement, the individual presses the button corresponding to the response choice to proceed to the next statement. Alternatively, script program 40 may specify a period of time that each statement is to be displayed before proceeding to the next statement. The remaining operation of the third embodiment is analogous to the operation of the preferred embodiment described above.

The multi-user capabilities of the present invention allow for the collection and tracking of patient data. Apparatuses 26 are connected to one or more servers 18. They are placed in a number of different public places, such as pharmacies, where they are accessible to a wide range of patients. Patient responses 42 and measurements 44 are received by apparatuses 26 in the manner described above. The data is then sent to server or servers 18 where it is collected and organized. Ideally, pharmaceutical companies or healthcare providers will use monitoring system 16 to gather patient response to their products or services. The companies or providers will send queries or script programs 40 to server 18, which will then send queries or script programs 40 to one or more apparatuses 26. After patients have answered the queries or attached their monitoring devices 28, server 18 will send the patient data back to the companies and providers.

Figure 22:
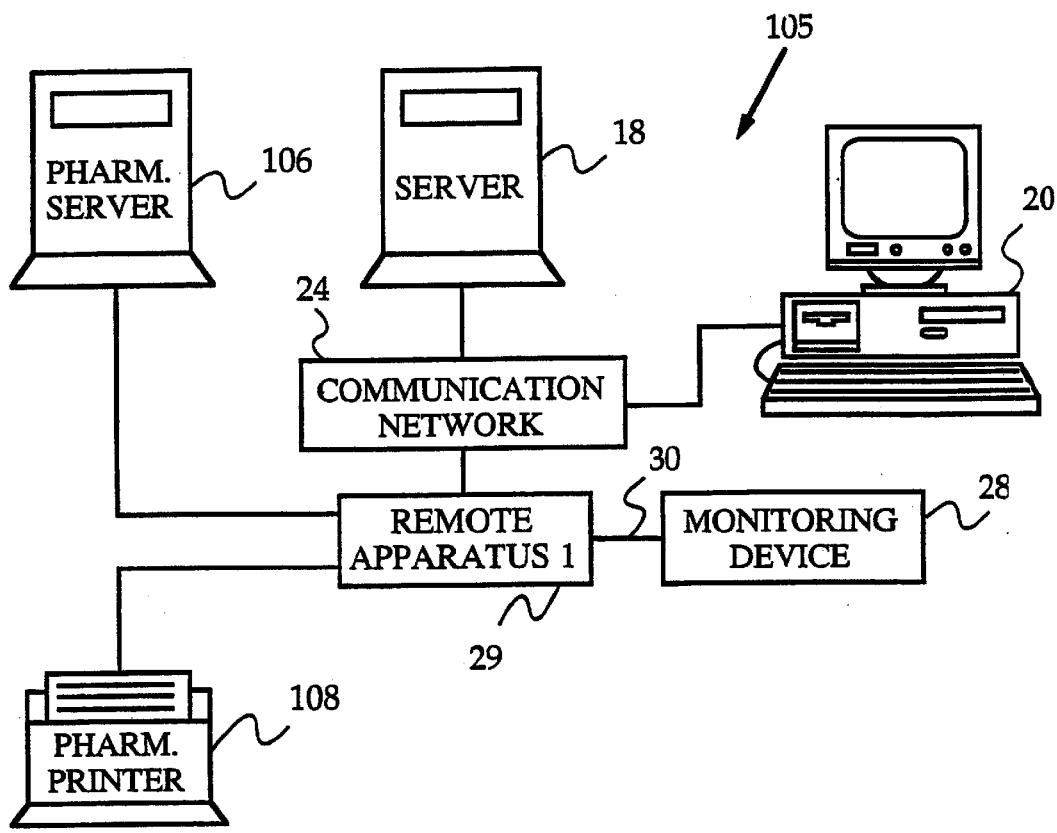
FIG. 22 is a block diagram of a networked system according to the data interception embodiment of the invention.

FIG. 22 shows how the present invention can be used in conjunction with a separate information system, such as a pharmacy information system. Patient data from the pharmacy information system 105 can be intercepted by the apparatus 29 in order to trigger the execution of script programs 40. In this embodiment, apparatus 29 is located in series between the pharmacy server 106 of pharmacy information system 105 and the pharmacy printer 108. Pharmacy information system 105 comprises pharmacy server 106, pharmacy workstation 107, and pharmacy printer 108. Patient data sent from pharmacy server 106 to pharmacy printer 108 must pass through apparatus 29. Apparatus 29 takes the patient data and sends it to server 18 of the system of the present invention. Server 18 uses patient data to determine which script program 40 to send to apparatus 29 for patient to answer. It is obvious that this method can be used to identify the patient to apparatus 29 and also server 18.

Alternatively, interception of patient data by apparatus 29 can be used to trigger printing of information on pharmacy printer 108. In this embodiment, apparatus 29 is again located in series between pharmacy server 106 of separate information system 105 and pharmacy printer 108. When apparatus 29 receives the patient data, it triggers a stored script program 40, which commands pharmacy printer 108 to print out information for the patient. This information differs in content from the patient data and is printed in addition to it. In addition, the patient data can also be sent to server 18 to trigger additional script program 40 which displays queries on display 64 of apparatus 29 to be answered by patient.

Figure 23:
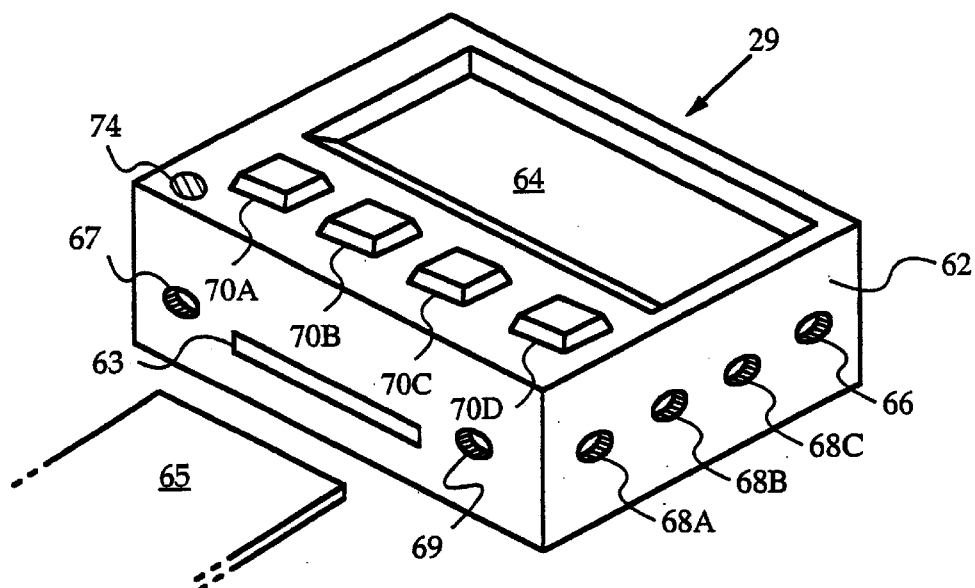
FIG. 23 is a perspective view of a remotely programmable apparatus of the system of FIG. 22.
Figure 24:
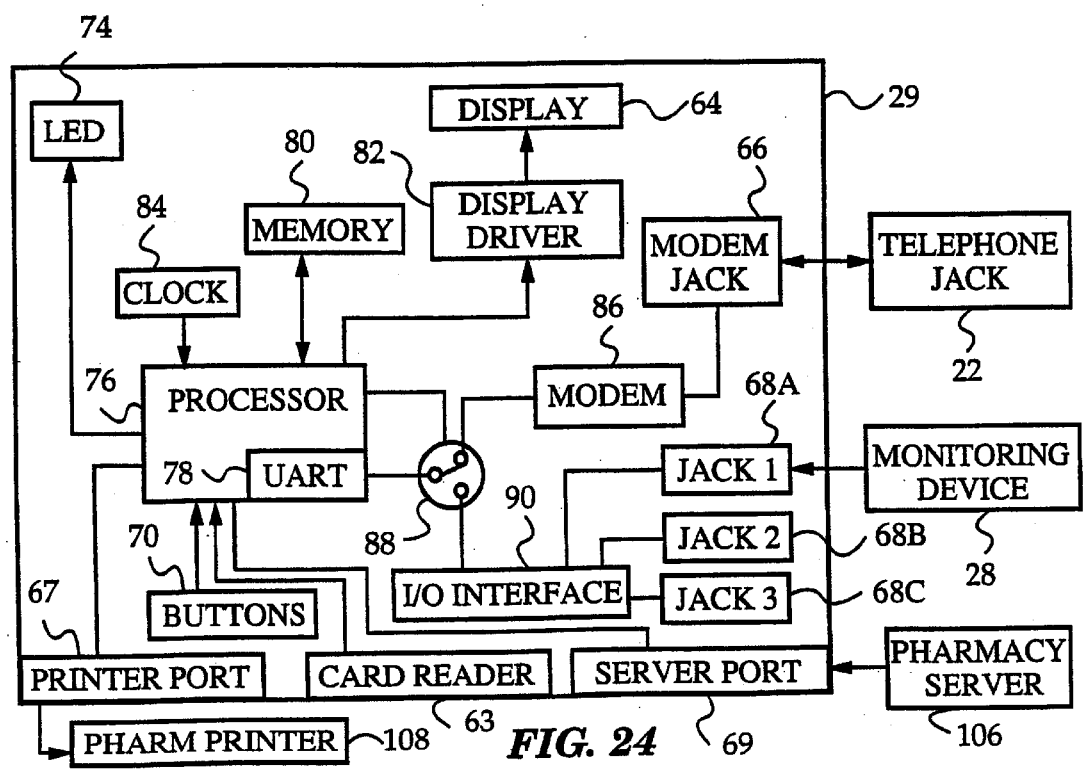
FIG. 24 is a block diagram illustrating the components of the apparatus of FIG. 23.

FIG. 23 shows a block diagram of apparatus 29 as used in this emnbodiment, while FIG. 24 shows a schematic block diagram illustrating the components of apparatus 29 in greater detail. FIGS. 23 and 24 are similar to FIGS. 3 and 4, except for the addition of a server port 69 in both figures. Server port 69 is used to connect apparatus 29 to pharmacy server 106. Server port 69 can receive a standard SCSI cable connection or a telephone cable connection, in which case it operates as a modem. Thus apparatus 29 can connect to server 18 through modem jack 66, pharmacy server 106 through server port 69, monitoring device 28 through device jacks 68A, 68B, and 68C, and pharmacy printer 108 through printer port 67.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the invention is not limited to the specific applications described. The system and method of the invention have many other applications both inside and outside the healthcare industry. For example, the system may also be used by insurance companies and medical clinics to conduct all types of surveys of patients. Retailers and service companies can conduct all types of surveys of consumers. Marketing firms can use the invention to do widespread market research. In addition, stores can use the invention to receive information from customers regarding their shopping tastes. An example of this application would be a bridal registry.

The invention may also be used for educational purposes, such as testing students remotely. Students can use the apparatus to take national standardized multiple-choice tests, such as the Graduate Record Examination (GRE). In addition, the invention can be used for financial purposes. Banks, utilities, credit card companies, etc. can send billing information from their servers to customers using the apparatuses. Customers can then authorize the institutions to transfer funds, pay their bills, etc.

Therefore, the scope of the invention should be determined not by the examples given, but by the appended claims and their legal equivalents.

What is claimed is:

1. A method for assisting a patient to comply with a therapeutic medical program, the method comprising the steps of:

inputting health data relating to the patient at prescribed times;

correlating the patient's health data with the therapeutic medical program using a relational database;

generating compliance data indicative of whether the patient is complying with the program; and motivating the patient to comply with a behavior modification program by:

providing medical information to the patient relating to the program;

presenting the patient with the compliance data to allow the patient to personally monitor compliance with the program;

signaling the patient to take action according to the program through an electronic interface integrated with the patient's daily schedule; and enabling the patient to retrieve the medical information, compliance data, and scheduling signals, and participate in one or more group support sessions and view the motivational media through a graphical electronic interface.

2. A multi-user remote health monitoring system comprising:

a computer, comprising a database and a first microprocessor coupled to the database, for composing a plurality of script programs according to a therapeutic medical program to query a patient at prescribed times;

a monitoring device for monitoring the patient's compliance with the program including:

an output interface for presenting queries to the patient to enter data;

an input interface allowing the patient to enter the queried data;

a second microprocessor for correlating the patient's entered data with the therapeutic medical program and generating compliance data indicative of the patient's progress toward achievement of the therapeutic medical program;

a plurality of script programs, accessible to the relational database and microprocessor, for motivating the patient to comply with the program comprising an integrated system of graphical system interfaces, the motivating means including:

means for enabling the patient to review the compliance data;

means for providing health information to the patient from a remote source; and an electronic calendar integrated with the therapeutic medical program for signaling the patient to take action pursuant to the behavior modification program wherein the calendar accesses the relational database and integrates requirements of the program with the patient's daily schedule.

3. The system of claim 2, wherein the motivating means include an electronic meeting room for linking the patient to a plurality of other patients having related behavior modification programs for facilitating group peer support sessions for compliance with the program.

4. The system of claim 2, wherein the motivating means include an means for providing motivational media presentations to the patient for encouraging the patient to comply with the program.

5. The system of claim 2, wherein the plurality of script programs comprises:

means for inputting preliminary health information relating to the patient;

means for presenting a plurality of suggested script programs from the database generated as a function of the preliminary health information;

means for selecting from the plurality of suggested script programs; and means for loading the script program into the monitoring device.

6. The system of claim 2, wherein the second microprocessor stores the compliance data in association with the patient's identity.

7. The system of claim 6, wherein the second microprocessor transmits the compliance data stored in association with the patient's identity to remote healthcare provider.

* * * * *

UNITED STATES PATENT AND TRADEMARK OFFICE
CERTIFICATE OF CORRECTION

PATENT NO.     : 6,381,577 B1
DATED          : April 30, 2002
INVENTOR(S)    : Stephen J. Brown It is certified that error appears in the above-identified patent and that said Letters Patent is hereby corrected as shown below:

<u>Title page,</u>
Item [63], Related U.S. Application Data, delete "878" and insert instead -- 478 --; and delete "Pat. No. 5,897,493." and replace with -- Pat. No. 5,897,493, which claims benefit from provisional 60/041,746, filed on March 28, 1997, and provisional application application No. 60/041,751, filed on March 28, 1997. --
Item [60], delete "Provisional application No. 60/041,746, filed on March 28, 1997, and provisional application No. 60/041,751, filed on March 28, 1997."

Signed and Sealed this

Twenty-fifth Day of November, 2003

JAMES E. ROGAN
*Director of the United States Patent and Trademark Office*